United States Patent
Khan

(10) Patent No.: US 9,932,347 B2
(45) Date of Patent: Apr. 3, 2018

(54) SPIRO-LACTAM NMDA RECEPTOR MODULATORS AND USES THEREOF

(71) Applicant: Aptinyx Inc., Evanston, IL (US)

(72) Inventor: M. Amin Khan, Evanston, IL (US)

(73) Assignee: Aptinyx Inc., Evanston, IL (US)

( * ) Notice: Subject to any disclaimer, the term of this patent is extended or adjusted under 35 U.S.C. 154(b) by 6 days.

(21) Appl. No.: 15/638,669

(22) Filed: Jun. 30, 2017

(65) Prior Publication Data

US 2017/0334922 A1 Nov. 23, 2017

Related U.S. Application Data

(63) Continuation of application No. PCT/US2017/033323, filed on May 18, 2017.

(60) Provisional application No. 62/338,767, filed on May 19, 2016.

(51) Int. Cl.
| | |
|---|---|
| *C07D 487/10* | (2006.01) |
| *A61K 31/4025* | (2006.01) |
| *A61K 38/00* | (2006.01) |
| *C07D 471/20* | (2006.01) |
| *C07K 16/00* | (2006.01) |

(52) U.S. Cl.
CPC ........ *C07D 487/10* (2013.01); *A61K 31/4025* (2013.01); *C07D 471/20* (2013.01); *A61K 38/00* (2013.01); *C07K 16/00* (2013.01)

(58) Field of Classification Search
CPC combination set(s) only.
See application file for complete search history.

(56) References Cited

U.S. PATENT DOCUMENTS

| | | | |
|---|---|---|---|
| 4,904,681 A | 2/1990 | Cordi et al. | |
| 4,959,493 A | 9/1990 | Ohfume et al. | |
| 5,061,721 A | 10/1991 | Cordi et al. | |
| 5,086,072 A | 2/1992 | Trullas et al. | |
| 5,166,136 A | 11/1992 | Ward et al. | |
| 5,168,103 A | 12/1992 | Kinney et al. | |
| 5,350,769 A | 9/1994 | Kasai et al. | |
| 5,523,323 A | 6/1996 | Maccecchini | |
| 5,605,911 A | 2/1997 | Olney et al. | |
| 5,648,259 A | 7/1997 | Mallet et al. | |
| 5,741,778 A | 4/1998 | Martin et al. | |
| 5,763,393 A | 6/1998 | Moskal et al. | |
| 5,804,550 A | 9/1998 | Bourguignon | |
| 5,902,815 A | 5/1999 | Olney et al. | |
| 5,952,389 A | 9/1999 | Fogel | |
| 5,959,075 A | 9/1999 | Lok et al. | |
| 6,007,841 A | 12/1999 | Caruso | |
| 6,025,471 A | 2/2000 | Deghenghi | |
| 6,107,271 A | 8/2000 | Moskal et al. | |
| 6,147,230 A | 11/2000 | Shimamoto et al. | |
| 6,197,820 B1 | 3/2001 | Sontheimer et al. | |
| 6,521,414 B2 | 2/2003 | Melcher et al. | |
| 6,541,453 B2 | 4/2003 | Oldham et al. | |
| 6,635,270 B2 | 10/2003 | Hong et al. | |
| 6,667,317 B2 | 12/2003 | Chenard et al. | |
| 6,821,985 B2 | 11/2004 | Chenard et al. | |
| 6,828,318 B2 | 12/2004 | Snape et al. | |
| 7,273,889 B2 | 9/2007 | Mermelstein et al. | |
| 7,884,080 B2 | 2/2011 | Aslanian et al. | |
| 8,492,340 B2 | 7/2013 | Moskal | |
| 9,504,670 B2 * | 11/2016 | Lowe, III | C07D 487/10 |
| 9,512,133 B2 | 12/2016 | Khan et al. | |
| 9,512,134 B2 * | 12/2016 | Lowe, III | C07D 487/10 |
| 9,579,304 B2 | 2/2017 | Lowe, III et al. | |
| 2002/0103335 A1 | 8/2002 | Oldham et al. | |
| 2003/0022253 A1 | 1/2003 | Moskal | |
| 2003/0064921 A1 | 4/2003 | Millhauser et al. | |
| 2003/0175734 A1 | 9/2003 | Kroes et al. | |
| 2005/0037433 A1 | 2/2005 | Nakanishi et al. | |
| 2005/0118286 A1 | 6/2005 | Suffin et al. | |
| 2006/0063707 A1 | 3/2006 | Baudry et al. | |
| 2006/0241046 A1 | 10/2006 | Olivera et al. | |
| 2007/0087404 A1 | 4/2007 | Stahl et al. | |
| 2007/0208001 A1 | 9/2007 | Zhuo et al. | |
| 2009/0221544 A1 | 9/2009 | Stein et al. | |
| 2010/0102616 A1 | 4/2010 | Yamasaki et al. | |
| 2011/0306586 A1 | 12/2011 | Khan et al. | |
| 2012/0295852 A1 | 11/2012 | Moskal | |
| 2013/0005662 A1 | 1/2013 | Moskal | |
| 2013/0035292 A1 | 2/2013 | Moskal et al. | |
| 2013/0053325 A1 | 2/2013 | Moskal et al. | |

(Continued)

FOREIGN PATENT DOCUMENTS

| | | |
|---|---|---|
| CN | 101066945 A | 11/2007 |
| CN | 101125817 A | 2/2008 |

(Continued)

OTHER PUBLICATIONS

Abbott AV et al., 'The Formalin Test: Scoring Properties of the First and Second Phases of the Pain Response in Rats,' Pain, Jan. 1995 (Jan. 1995), 60(1):91-102.

Abramets, II 'Neurophysiological and Neurochemical Aspects of the Effects of Antidepressants and Mood Stabilizers,' Neurophysiol, Jan. 2008 (Jan. 2008), 40(1):64-78.

Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.

Anonymous, Database Accession No. 1031928-30-9, Database Registry [Online] Chemical Abstracts Service, Columbus, Ohio, US; Jul. 1, 2008 (Jul. 1, 2008), XP002668992.

Anonymous, Database Accession No. 1053605-89-2, Database Registry [Online] Chemical Abstracts Service, Columbus, Ohio, US; Sep. 28, 2008 (Sep. 28, 2008), XP002668993.

(Continued)

*Primary Examiner* — Amanda L Aguirre
(74) *Attorney, Agent, or Firm* — Goodwin Procter LLP

(57) ABSTRACT

Disclosed are compounds having enhanced potency in the modulation of NMDA receptor activity. Such compounds can be used in the treatment of conditions such as depression and related disorders. Orally available formulations and other pharmaceutically acceptable delivery forms of the compounds, including intravenous formulations, are also disclosed.

6 Claims, 18 Drawing Sheets

(56) References Cited

U.S. PATENT DOCUMENTS

| | | |
|---|---|---|
| 2013/0310323 A1 | 11/2013 | Moskal |
| 2013/0316954 A1 | 11/2013 | Moskal |
| 2014/0107037 A1 | 4/2014 | Moskal |
| 2015/0051262 A1 | 2/2015 | Khan et al. |
| 2015/0105364 A1 | 4/2015 | Khan et al. |
| 2015/0336969 A1 | 11/2015 | Khan et al. |
| 2015/0368252 A1 | 12/2015 | Lowe, III et al. |
| 2015/0368253 A1 | 12/2015 | Lowe, III et al. |
| 2015/0368254 A1 | 12/2015 | Lowe, III et al. |
| 2015/0376195 A1 | 12/2015 | Lowe, III et al. |

FOREIGN PATENT DOCUMENTS

| | | | |
|---|---|---|---|
| CN | 103974712 A | 8/2014 | |
| CN | 104321071 A | 1/2015 | |
| EP | 2542254 A1 | 1/2013 | |
| EP | 2771021 | 5/2013 | |
| JP | 2013519683 A | 5/2013 | |
| JP | 2014520072 A | 8/2014 | |
| RU | 2039035 C1 | 7/1995 | |
| WO | WO-1996032105 A1 | 10/1996 | |
| WO | WO-1997/043306 A1 | 11/1997 | |
| WO | WO-1999/024584 A1 | 5/1999 | |
| WO | WO-1999/051985 A1 | 10/1999 | |
| WO | WO-2000/028090 A2 | 5/2000 | |
| WO | WO-2001/36685 A2 | 5/2001 | |
| WO | WO-2001/96606 A2 | 12/2001 | |
| WO | WO-2001/98367 A2 | 12/2001 | |
| WO | WO-2002/47535 A2 | 6/2002 | |
| WO | WO-2002/072609 A2 | 9/2002 | |
| WO | WO-2003/010540 A1 | 2/2003 | |
| WO | WO-2004/005293 A3 | 5/2004 | |
| WO | WO-2005/020973 A2 | 3/2005 | |
| WO | WO-2005/035535 A1 | 4/2005 | |
| WO | WO-2007088041 A1 | 8/2007 | |
| WO | WO-2007103719 A2 | 9/2007 | |
| WO | WO-2009/039390 A2 | 3/2009 | |
| WO | WO-2009/105718 A1 | 8/2009 | |
| WO | WO-2010/015545 A1 | 2/2010 | |
| WO | WO-2010/033757 A1 | 3/2010 | |
| WO | WO-2010/065709 A2 | 6/2010 | |
| WO | WO-2010/102616 A1 | 9/2010 | |
| WO | WO-2011/003064 A2 | 1/2011 | |
| WO | WO-2011/044089 A2 | 4/2011 | |
| WO | WO-2011/100585 A1 | 8/2011 | |
| WO | WO-2012/149389 A2 | 11/2012 | |
| WO | WO-2013/001448 A1 | 1/2013 | |
| WO | WO-2013/014448 A1 | 1/2013 | |
| WO | WO-2013/063120 A2 | 5/2013 | |
| WO | WO-2014/011590 A2 | 1/2014 | |
| WO | WO-2014/120783 A1 | 8/2014 | |
| WO | WO-2014/120784 A1 | 8/2014 | |
| WO | WO-2014/120786 A1 | 8/2014 | |
| WO | WO-2014/120789 A1 | 8/2014 | |
| WO | WO-2014/120800 A1 | 8/2014 | |
| WO | WO 2014120783 A1 * | 8/2014 | ........... C07D 487/10 |

OTHER PUBLICATIONS

Anonymous, NCBI Submission NM_000149, '*Homo sapiens* Fucosyltransferase 3 (galactoside 3(4)-L-fucosyltransferase, Lewis Blood Group)(FUT3), Transcript Variant 1, mRNA,' 1990 (1990), Retrieved from the internet; <<URL:http://www.ncbi.nlm.nih.gov/nuccore/148277008>>, pp. 1-5.

Anonymous, NCBI Submission NM_001276, '*Homo sapiens* Chitinase 3-like 1 (cartilage glycoprotein-39)(CHI3L1), mRNA,' 11989 (1989), Retrieved from the internet; <URL:http://www.ncbi.nlm.nih.gov/nuccore/144226250>, pp. 1-5.

Anonymous, NCBI Submission NM_030979.1, '*Homo sapiens* poly(A) Binding Protein, Cytoplasmic 3 (PABPC3), mRNA,' 2003 (2003), Retrieved from the internet; <URL:http://www.ncbi.nlm.nih.gov/nuccore/13569957>, pp. 1.

Anonymous, NCBI Submission NM_173216, '*Homo sapiens* ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Bennett GJ and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.

Burch RM et al., 'GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), pp. 1 (Poster #unknown).

Burgdorf JS et al., 'Neurobiology of 50-kHz Ultrasonic Vocalizations in Rats: Electrode, Lesion, and Pharmacology Studies,' Behav Brain Res, Mar. 19, 2007 (Mar. 19, 2007) (ePub), 182(2):274-83.

Burgdorf JS et al., 'The Antidepressant and Anxiolytic Properties of GLYX-13: A Novel NMDA Receptor Glycine Site Functional Partial Agonist,' *ACNP 2010 Meeting*, Dec. 6, 2010 (Dec. 6, 2010), pp. 1 (Poster #198).

Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.

Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.

Burgdorf JS et al., 'Uncovering the Molecular Basis of Positive Affect Using Rough-and-Tumble Play in Rats: A Role for the NMDA Receptor and Implications for Depression,' Neuroscience, Jul. 14, 2010, (Jul. 14, 2010) (ePub), 168(3):769-77.

Burgdorf JS et al., 'Uncovering the Molecular Basis of Positive Affect Using Rough-and-Tumble Play in Rats: A Role for the NMDA Receptor and Implications for Depression,' Neuroscience 38th Annual Meeting, Washington DC, Nov. 17, 2008 (Nov. 17, 2008), pp. 1-2 (Poster #393.1/UU11) [Electronically available Sep. 2008].

Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4):174-80.

Coates C et al., 'Product Class 9: Beta-Lactams,' *Science of Synthesis*, Georg Thieme Verlag KG, Stuttgart, DE (Pub), 2000 (2000), 21:609-46.

Cremonesi G et al., 'Enantiomerically Pure Polyheterocyclic Spiro-beta-Lactams from trans-4-Hydroxy-L-proline,' J Org Chem, Mar. 19, 2010 (Mar. 3, 2010), 75(6):2010-7.

Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.

Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.

Del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.

Duman RS, 'Pathophysiology of Depression: The Concept of Synaptic Plasticity,' Eur Psychiatry, Jul. 2002 (Jul. 2002), 17(Suppl 3):306-10.

Erick M Carreira and Lisbet Kvaerno, Classics in Stereoselective Synthesis, (1st ed. 2009), Wiley-Vch Verlag GmbH & Co. KGaA, Weinham, DE (Publ), pp. 19-102 ISBN: 978-3-527-32452-1.

(56) References Cited

OTHER PUBLICATIONS

European Patent Office, Supplementary European Search Report (Form 1503) for EP 09 81 5233 (Fink D), completed at Munich DE on Feb. 8, 2012 (Feb. 8, 2012) pp. 1-3.
European Patent Office, Supplementary European Search Report (form 1503) for EP 10 82 2514 (Fink D), completed at Munich DE on Feb. 1, 2013 (Feb. 1, 2013) pp. 1-2.
Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.
Foster AC and Fagg GE, 'Neurobiology: Taking Apart NMDA Receptors,' Nature, Oct. 1, 1987 (Oct. 1, 1987), 329(6138):395-6.
Golik U, 'Synthesis of Malonimide Derivatives as Potential Penicillin Analogs,' J Heterocyl Chem, Feb. 1972 (Feb. 1972), 9(1):21-4.
Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.
Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.
Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.
Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.
Haring R et al., 'Multiple Mode of Binding of Phencyclidines: High Affinity Association Between Phencyclidine Receptors in Rat Brain and a Monovalent Ion-Sensitive Polypeptide,' Biochem Biophys Res Commun, Jan. 30, 1987 (Jan. 30, 1987), 142(2):501-10.
Holderbach R et al., 'Enhanced Long-Term Synaptic Depression in an Animal Model of Depression,' Biol Psychiatry, Dec. 4, 2006 (Dec. 4, 2006) (ePub), 62(1):92-100.
International Searching Authority, International Search Report (ISA/210) for Application No. PCT/US08/77045, (Young LW), completed on Mar. 28, 2009 (Mar. 28, 2009) and dated Apr. 29, 2009 (Apr. 29, 2009), pp. 1-3.
International Searching Authority, International Search Report (ISA/210) for Application No. PCT/US09/57401, (Young LW), completed Dec. 6, 2009 (Dec. 6, 2009) and dated Dec. 24, 2009 (Dec. 24, 2009), pp. 1-2.
International Searching Authority, International Search Report (ISA/210) for Application No. PCT/US09/66536, (Kang YJ), completed Aug. 9, 2010 (Aug. 9, 2010) and dated Aug. 9, 2010 (Aug. 9, 2010), pp. 1-5.
International Searching Authority, International Search Report (ISA/210) for Application No. PCT/US2014/013619, (Wolf C), completed Mar. 6, 2014 (Mar. 6, 2014) and dated Mar. 20, 2014 (Mar. 20, 2014), pp. 1-3.
International Searching Authority, International Search Report (ISA/210) for Application No. PCT/US2014/013621, (Wolf C), completed Feb. 27, 2014 (Feb. 27, 2014) and dated Mar. 13, 2014 (Mar. 13, 2014), pp. 1-2.
International Searching Authority, International Search Report (ISA/210) for Application No. PCT/US2014/013623, (Wolf C), completed Mar. 3, 2014 (Mar. 3, 2014) and dated Mar. 13, 2014 (Mar. 13, 2014), pp. 1-3.
International Searching Authority, International Search Report (ISA/210) for Application No. PCT/US2014/013626, (Rudolf M), completed Mar. 10, 2014 (Mar. 10, 2014) and dated Mar. 18, 2014 (Mar. 18, 2014), pp. 1-4.
International Searching Authority, International Search Report (ISA/210) for Application No. PCT/US2014/013639, (Wolf C), completed Feb. 28, 2014 (Feb. 28, 2014) and dated Mar. 13, 2014 (Mar. 13, 2014), pp. 1-3.
International Searching Authority, Written Opinion of Application No. PCT/US2008/077045 (ISA/237), (Young LW), completed Mar. 28, 2009 (Mar. 24, 2009) and dated Mar. 24, 2010 (Mar. 24, 2010), pp. 1-8.
International Searching Authority, Written Opinion of Application No. PCT/US2009/057401 (ISA/237), (Young LW), completed Dec. 6, 2009 (Dec. 6, 2009) and dated Mar. 22, 2011 (Mar. 22, 2011), pp. 1-6.
International Searching Authority, Written Opinion of Application No. PCT/US2009/066536 (ISA/237), (Kang YJ), completed Aug. 9, 2010 (Aug. 9, 2010) and dated Jun. 7, 2011 (Jun. 7, 2011), pp. 1-8.
International Searching Authority, Written Opinion of Application No. PCT/US2014/013619 (ISA/237), (Wolf C), completed Mar. 6, 2014 (Mar. 6, 2014) and dated Aug. 4, 2015 (Aug. 4, 2015), pp. 1-4.
International Searching Authority, Written Opinion of Application No. PCT/US2014/013621 (ISA/237), (Wolf C), completed Feb. 27, 2014 (Feb. 27, 2014) and dated Aug. 4, 2015 (Aug. 4, 2015), pp. 1-6.
International Searching Authority, Written Opinion of Application No. PCT/US2014/013623 (ISA/237), (Wolf C), completed Mar. 3, 2014 (Mar. 6, 2014) and dated Aug. 4, 2015 (Aug. 4, 2015), pp. 1-4.
International Searching Authority, Written Opinion of Application No. PCT/US2014/013626 (ISA/237), (Rudolf M, completed Mar. 10, 2014 (Mar. 10, 2014) and dated Aug. 4, 2015 (Aug. 4, 2015), pp. 1-6.
International Searching Authority, Written Opinion of Application No. PCT/US2014/013639 (ISA/237), (Wolf C), completed Feb. 28, 2014 (Feb. 28, 2014) and dated Aug. 4, 2015 (Aug. 4, 2015), pp. 1-4.
Johnson JA et al., 'The Preparation of a Double Metallahelicate Containing 28 Copper Atoms,' Angew Chem Int Ed Engl, Feb. 3, 2003 (Feb. 3, 2003), 42(5):546-9.
Johnson KM and Jones SM, 'Neuropharmacolgy of Phencyclidine: Basic Mechanisms and Therapeutic Potential,' Annu Rev Pharmacol Toxicol, 1990 (1990), 30:707-50.
Khasanov AB et al., 'Novel Asymmetric Approach to Proline-Derived Spiro-beta-Lactams,' J Org Chem., Aug. 20, 2004 (Aug. 20, 2004), 69(17):5766-9.
Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.
Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.
Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.
Kroes RA et al., 'Development of a Novel Glycobiologic Therapy for Glioblastoma,' Neuro-oncol, Oct. 2006 (Oct. 2006), 8(4):397-8, (Abstract #CB-14).
Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).
Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep.-Oct. 1999), 7(3):125-43.
Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).
Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.
Lynch G et al., 'Synaptic Pasticity in Early Aging,' Ageing Res Rev, Aug. 28, 2006 (Aug. 28, 2006) (ePub), 5(3):255-80.
Macias A et al., 'Diastereoselective [2+2]-Cycloaddition Reactions of Unsymmetrical Cyclic Ketenes with Imines: Synthesis of Modi-

(56) References Cited

OTHER PUBLICATIONS fied Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.

Macias A et al., 'Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands,' Tetrahedron Lett, Jun. 2004 (Jun. 2004), 45(24):4657-60.

Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.

Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.

McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.

Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.

Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.

Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).

Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.

Moskal JR et al., 'A Novel Approach to Unlocking the Therapeutic Potential of the NMDA Receptor,' Vital Signs e-Magazine, Sep. 2010 (Sep. 2010), pp. 1-2.

Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.

Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.

Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).

Myers SM and Johnson CP, 'Management of Children with Autism Spectrum Disorders,' Pediatrics, Oct. 29, 2007 (Oct. 29, 2007) (ePub), 120(5):1162-82.

Narahashi T et al., 'Mechanisms of Action of Cognitive Enhancers on Neuroreceptors,' Biol Pharm Bull, Nov. 2004 (Nov. 2004), 27(11):1701-6.

Overman LE and Osawa T, 'A Convenient Synthesis of 4-Unsubstituted beta-Lactams,' J Am Chem Soc, Mar. 1985 (Mar. 1985), 107(6):1698-701.

Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.

Pittenger C et al., 'The NMDA Receptor as a Therapeutic Target in Major Depressive Disorder,' CNS Neurol Disord Targets, Apr. 2007 (Apr. 2007), 6(2):101-15.

Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.

Ransom RW and Stec NL, 'Cooperative Modulation of [3H]MK-801 Binding to the N-Methyl-d-Asparate Receptor-Ion Channel Complex by l-Glumate, Glycine, and Polyamines,' J Neurochem, Sep. 1988 (Sep. 1988), 51(3):830-6.

Rasmusson GH et al., '6-Substituted Penicillin Derivatives,' Tetrahedron Lett, 1973 (1973), 14(2):145-8.

Rautio J et al., 'Prodrugs: Design and Clinical Applications,' Nat Rev Drug Discov, Mar. 2008 (Mar. 2008), 7(3):255-70.

Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.

Shankar GM and Walsh DM, 'Alzheimer's Disease: Synaptic Dysfunction and A-beta,' Mol Neurodegener, Nov. 23, 2009 (Nov. 23, 2009), 4:48-61.

Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.

Simplício AL et a;., 'Prodrugs for Amines,' Molecules, Mar. 2008 (Mar. 2008), 13(3):519-47.

Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.

Stanton PK et al., 'Neuroprotection by a Novel NMDAR Functional Glycine Site Partial Agonist, GLYX-13,' Neuroreport, Aug. 26, 2009 (Aug. 26, 2009), 20(13):1193-7.

Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.

Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.

Turturro A et al., 'Growth Curves and Survival Characteristics of the Animals Used in the Biomarkers of Aging Program,' J Gerentol A Biol Sci Med Sci, Nov. 1999 (Nov. 1999), 54A(11):B492-B501.

Various, *The NMDA Receptor*, (2nd ed. 1994), GL Collingridge and JC Watkins Eds., Oxford University Press, Inc., New York, New York US (Publ), pp. 1-479 ISBN: 0-19-262371-0.

Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10):1061-3.

Wood PL, 'The NMDA Receptor Complex: A Long and Winding Road to Therapeutics,' IDrugs, Mar. 2005 (Mar. 2005), 8(3):229-35.

Wood SG et al., 'Tetrapeptide Inhibitors of the IgA1 Proteinases from Type I Neisseria gonorrhoeae,' J Med Chem, Oct. 1989 (Oct. 1989), 32(10):2407-11.

Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.

Singapore Search Report and Written Opinion issued for corresponding Singapore application No. 11201505860X, dated Apr. 18, 2016.

Singapore Search Report and Written Opinion issued for corresponding Singapore application No. 11201505942Y, dated Mar. 22, 2016.

Singapore Search Report and Written Opinion issued for corresponding Singapore application No. 11201505934X, dated Apr. 27, 2016.

Singapore Search Report and Written Opinion issued for corresponding Singapore application No. 11201505862T, dated Apr. 18, 2016.

Singapore Search Report and Written Opinion issued for corresponding Singapore application No. 11201505937S, dated May 5, 2016.

(56) References Cited

OTHER PUBLICATIONS

Export Data for 3 hydroxy 2 5 sulfonyl oxo2 5 diazaspiro, Apr. 22, 2016, Feb. 3, 2016, Jan. 30, 2016 and Mar. 26, 2015.
International Search Report for PCT/US2017/033323 dated Jul. 17, 2017 (5 pages).
Written Opinion for PCT/US2017/03333 dated Jul. 17, 2017 (7 pages).
International Search Report for PCT/US2017/033326 dated Jul. 10, 2017 (5 pages).
Written Opinion for PCT/US2017/033326 dated Jul. 10, 2017 (7 pages).

\* cited by examiner

| IN VITRO MN | |
|---|---|
| Test Concentration | Cytotoxicity (% of Control) |
| 6.00 E-07 | 88% |
| 1.20 E-06 | 88% |
| 2.50 E-06 | 77% |
| 5.00 E-06 | 86% |
| 1.00 E-05 | 87% |
| 2.50 E-05 | 86% |
| 5.00 E-05 | 88% |
| 1.00 E-04 | 90% |
| 6.00 E-07 | 106% |
| 1.20 E-06 | 104% |
| 2.50 E-06 | 103% |
| 5.00 E-06 | 101% |
| 1.00 E-05 | 99% |
| 2.50 E-05 | 98% |
| 5.00 E-05 | 99% |
| 1.00 E-04 | 99% |
| 6.00 E-07 | 97% |
| 1.20 E-06 | 93% |
| 2.50 E-06 | 93% |
| 5.00 E-06 | 95% |
| 1.00 E-05 | 96% |
| 2.50 E-05 | 94% |
| 5.00 E-05 | 98% |
| 1.00 E-04 | 99% |
| 6.00 E-07 | 108% |
| 1.20 E-06 | 99% |
| 2.50 E-06 | 102% |
| 5.00 E-06 | 96% |
| 1.00 E-05 | 96% |
| 2.50 E-05 | 115% |
| 5.00 E-05 | 118% |
| 1.00 E-04 | 104% |

| AMES | |
|---|---|
| Test Concentration | Positive Significance (- to +++) |
| 5.00 E-06 | - |
| 1.00 E-05 | - |
| 5.00 E-05 | - |
| 1.00 E-04 | - |
| 5.00 E-06 | - |
| 1.00 E-05 | - |
| 5.00 E-05 | - |
| 1.00 E-04 | - |
| 5.00 E-06 | - |
| 1.00 E-05 | - |
| 5.00 E-05 | - |
| 1.00 E-04 | - |
| 5.00 E-06 | - |
| 1.00 E-05 | - |
| 5.00 E-05 | - |
| 1.00 E-04 | - |
| 5.00 E-06 | - |
| 1.00 E-05 | - |
| 5.00 E-05 | - |
| 1.00 E-04 | - |
| 5.00 E-06 | - |
| 1.00 E-05 | - |
| 5.00 E-05 | - |
| 1.00 E-04 | - |
| 5.00 E-06 | - |
| 1.00 E-05 | - |
| 5.00 E-05 | - |
| 1.00 E-04 | - |
| 5.00 E-06 | - |
| 1.00 E-05 | - |
| 5.00 E-05 | - |
| 1.00 E-04 | - |

| HERG |
|---|
| % Inhibition of Control Specific Binding |
| -7.3% |

FIG. 9

| IN VITRO MN | | AMES | |
|---|---|---|---|
| Test Concentration | Cytotoxicity (% of Control) | Test Concentration | Positive Significance (- to +++) |
| 6.00 E-07 | 88% | 5.00 E-06 | - |
| 1.20 E-06 | 83% | 1.00 E-05 | - |
| 2.50 E-06 | 73% | 5.00 E-05 | - |
| 5.00 E-06 | 95% | 1.00 E-04 | - |
| 1.00 E-05 | 78% | 5.00 E-06 | - |
| 2.50 E-05 | 86% | 1.00 E-05 | - |
| 5.00 E-05 | 86% | 5.00 E-05 | - |
| 1.00 E-04 | 91% | 1.00 E-04 | - |
| 6.00 E-07 | 104% | 5.00 E-06 | - |
| 1.20 E-06 | 104% | 1.00 E-05 | + |
| 2.50 E-06 | 102% | 5.00 E-05 | - |
| 5.00 E-06 | 106% | 1.00 E-04 | - |
| 1.00 E-05 | 97% | 5.00 E-06 | - |
| 2.50 E-05 | 98% | 1.00 E-05 | - |
| 5.00 E-05 | 103% | 5.00 E-05 | - |
| 1.00 E-04 | 96% | 1.00 E-04 | - |
| 6.00 E-07 | 90% | 5.00 E-06 | - |
| 1.20 E-06 | 91% | 1.00 E-05 | - |
| 2.50 E-06 | 96% | 5.00 E-05 | - |
| 5.00 E-06 | 96% | 1.00 E-04 | - |
| 1.00 E-05 | 103% | 5.00 E-06 | - |
| 2.50 E-05 | 99% | 1.00 E-05 | - |
| 5.00 E-05 | 98% | 5.00 E-05 | - |
| 1.00 E-04 | 103% | 1.00 E-04 | - |
| 6.00 E-07 | 110% | 5.00 E-06 | - |
| 1.20 E-06 | 101% | 1.00 E-05 | - |
| 2.50 E-06 | 109% | 5.00 E-05 | - |
| 5.00 E-06 | 107% | 1.00 E-04 | - |
| 1.00 E-05 | 101% | 5.00 E-06 | - |
| 2.50 E-05 | 102% | 1.00 E-05 | - |
| 5.00 E-05 | 107% | 5.00 E-05 | - |
| 1.00 E-04 | 123% | 1.00 E-04 | - |

| HERG |
|---|
| % Inhibition of Control Specific Binding |
| -4.6% |

FIG. 10

SPIRO-LACTAM NMDA RECEPTOR MODULATORS AND USES THEREOF

CROSS REFERENCE TO RELATED APPLICATIONS

This application is a continuation application of PCT/US2017/033323, filed May 18, 2017, which claims priority to and the benefit of U.S. Provisional Patent Application No. 62/338,767, filed on May 19, 2016; the contents of each of which are hereby incorporated by reference herein in their entirety.

BACKGROUND

An N-methyl-d-aspartate ("NMDA") receptor is a post-synaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's and Parkinson's related conditions such as dyskinesia and L-dopa induced dyskinesia and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "functional partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{++}$ flow through the receptor channel.

A need continues to exist in the art for novel and more specific/potent compounds that are capable of binding the glycine binding site of NMDA receptors, and provide pharmaceutical benefits. In addition, a need continues to exist in the medical arts for orally deliverable forms of such compounds.

SUMMARY

The present disclosure provides compounds that can be NMDA modulators, for example, partial agonists of NMDA. More specifically, the present disclosure provides a compound having the formula:

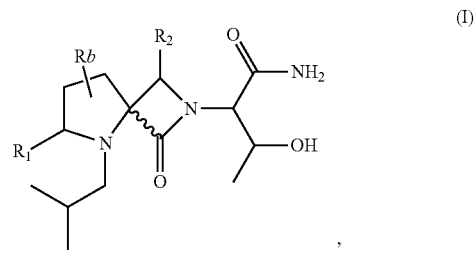

(I)

or a stereoisomer, an N-oxide, and/or a pharmaceutically acceptable salt thereof, where $R^b$ is selected from the group consisting of hydrogen, halogen, hydroxyl, cyano, and $C_1$-$C_6$ alkyl; $R^1$ is selected from the group consisting of hydrogen, halogen, and $C_1$-$C_6$ alkyl; and $R^2$ is selected from the group consisting of hydrogen, halogen, and $C_1$-$C_6$ alkyl.

Also provided herein are pharmaceutical compositions including a disclosed compound; and a pharmaceutically acceptable excipient. Such a composition can be suitable for oral or intravenous administration to a patient.

In some embodiments, the compounds described herein bind to NMDA receptor subtypes. In some embodiments, the compounds described herein bind to one subtype and not another.

In another aspect, a method of treating a condition selected from the group consisting of autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder, phobia, post-traumatic stress syndrome, a behavior disorder, an impulse control disorder, a substance abuse disorder, a sleep disorder, a memory disorder, a learning disorder, urinary incontinence, multiple system atrophy, progressive supra-nuclear palsy, Friedrich's ataxia, Down's syndrome, fragilexsyndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, fibromyalgia, acute neuropathic pain, and chronic neuropathic pain, in a patient in need thereof is provided. Such methods can include administering to a patient a pharmaceutically effective amount of a disclosed compound, or a pharmaceutically acceptable salt, a stereoisomer, an N-oxides, and/or a hydrate thereof.

In some embodiments, a method includes treating depression. For example, depression can include one or more of major depressive disorder, dysthymic disorder, psychotic depression, postpartum depression, seasonal affective disorder, bipolar disorder, mood disorder, or depression caused by a chronic medical condition. In certain embodiments, a method can treat schizophrenia. Such schizophrenia can be paranoid type schizophrenia, disorganized type schizophrenia, catatonic type schizophrenia, undifferentiated type schizophrenia, residual type schizophrenia, post-schizophrenic depression, or simple schizophrenia.

BRIEF DESCRIPTION OF THE DRAWINGS

FIG. 9 depicts the results from the in vitro MN, Ames, and hERG assays for compound A.

FIG. 10 depicts the results from the in vitro MN, Ames, and hERG assays for compound B.

DETAILED DESCRIPTION

Figure 1:
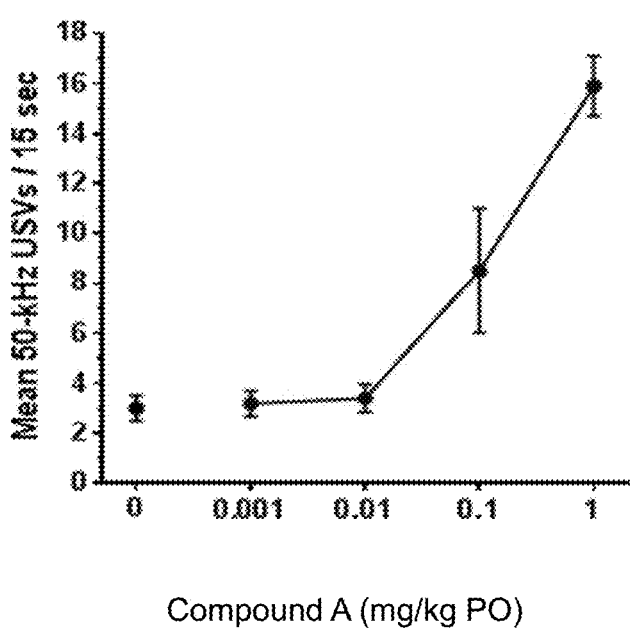
FIG. 1 depicts the mean 50-kHz USV data for compound A in a positive emotional learning (PEL) model.

This disclosure is generally directed to compounds that are capable of modulating NMDA, for example, NMDA antagonists or partial agonists, and compositions and/or methods of using the disclosed compounds. It should be appreciated that the disclosed compounds may modulate other protein targets and/or NMDA receptor subtypes.

The term "alkyl," as used herein, refers to a saturated straight-chain or branched hydrocarbon, such as a straight-chain or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. For example, "$C_1$-$C_6$ alkyl" refers to a straight-chain or branched saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl.

The term "cyano," as used herein, refers to the radical —CN.

The terms "halo" or "halogen," as used herein, refer to fluoro (F), chloro (Cl), bromo (Br), and/or iodo (I).

The terms "hydroxy" and "hydroxyl," as used herein, refer to the radical —OH.

The term "compound," as used herein, refers to the compound itself and its pharmaceutically acceptable salts, hydrates, esters and N-oxides including its various stereoisomers and its isotopically-labelled forms, unless otherwise understood from the context of the description or expressly limited to one particular form of the compound, i.e., the compound itself, a specific stereoisomer and/or isotopically-labelled compound, or a pharmaceutically acceptable salt, a hydrate, an ester, or an N-oxide thereof. It should be understood that a compound can refer to a pharmaceutically acceptable salt, or a hydrate, an ester or an N-oxide of a stereoisomer of the compound and/or an isotopically-labelled compound.

The term "moiety," as used herein, refers to a portion of a compound or molecule.

The compounds of the disclosure can contain one or more chiral centers and/or double bonds and therefore, can exist as stereoisomers, such as geometric isomers, and enantiomers or diastereomers. The term "stereoisomers," when used herein, consists of all geometric isomers, enantiomers and/or diastereomers of the compound. For example, when a compound is shown with specific chiral center(s), the compound depicted without such chirality at that and other chiral centers of the compound are within the scope of the present disclosure, i.e., the compound depicted in two-dimensions with "flat" or "straight" bonds rather than in three dimensions, for example, with solid or dashed wedge bonds. Stereospecific compounds may be designated by the symbols "R" or "S," depending on the configuration of substituents around the stereogenic carbon atom. The present disclosure encompasses all the various stereoisomers of these compounds and mixtures thereof. Mixtures of enantiomers or diastereomers can be designated "(±)" in nomenclature, but a skilled artisan will recognize that a structure can denote a chiral center implicitly. It is understood that graphical depictions of chemical structures, for example, generic chemical structures, encompass all stereoisomeric forms of the specified compounds, unless indicated otherwise.

As discussed herein, the compounds of the present disclosure can have a plurality of chiral centers. Each chiral center may be independently R, S, or any mixture of R and S. For example, in some embodiments, a chiral center may have an R:S ratio of between about 100:0 and about 50:50 ("racemate"), between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, or about 50:50. Formulations of the disclosed compounds comprising a greater ratio of one or more isomers (i.e., R and/or S) may possess enhanced therapeutic characteristic relative to racemic formulations of a disclosed compounds or mixture of compounds.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, *Classics in Stereoselective Synthesis*, Wiley-VCH: Weinheim, 2009.

Geometric isomers, resulting from the arrangement of substituents around a carbon-carbon double bond or arrangement of substituents around a cycloalkyl or heterocyclic ring, can also exist in the compounds of the present disclosure. The symbol ═ denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The disclosure also embraces isotopically-labeled compounds which are identical to those compounds recited herein, except that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2H$ ("D"), $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound described herein can have one or more H atoms replaced with deuterium.

Certain isotopically-labeled compounds (e.g., those labeled with $^3H$ and $^{14}C$) can be useful in compound and/or substrate tissue distribution assays. Tritiated (i.e., $^3H$) and carbon-14 (i.e., $^{14}C$) isotopes can be particularly preferred for their ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements) and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

The phrases "pharmaceutically acceptable" or "pharmacologically acceptable," as used herein, refer to compounds, molecular entities, compositions, materials and/or dosage forms that do not produce an adverse, allergic or other untoward reaction when administered to an animal, or a human, as appropriate. For human administration, preparations should meet sterility, pyrogenicity, general safety and purity standards as required by FDA Office of Biologics standards.

The phrases "pharmaceutically acceptable carrier" and "pharmaceutically acceptable excipient," as used herein, refer to any and all solvents, dispersion media, coatings, isotonic and absorption delaying agents, and the like, that are compatible with pharmaceutical administration. Pharmaceutical acceptable carriers can include phosphate buffered saline solution, water, emulsions (e.g., such as an oil/water or water/oil emulsions), and various types of wetting agents. The compositions also can include stabilizers and preservatives.

The phrase "pharmaceutical composition," as used herein, refers to a composition comprising at least one compound as disclosed herein formulated together with one or more pharmaceutically acceptable carriers. Pharmaceutical compositions can also contain other active compounds providing supplemental, additional, or enhanced therapeutic functions.

The terms "individual," "patient," and "subject," as used herein, are used interchangeably and include any animal, including mammals, preferably mice, rats, other rodents, rabbits, dogs, cats, swine, cattle, sheep, horses, or primates, and more preferably, humans. The compounds described in the disclosure can be administered to a mammal, such as a human, but can also be administered to other mammals such as an animal in need of veterinary treatment, for example, domestic animals (e.g., dogs, cats, and the like), farm animals (e.g., cows, sheep, pigs, horses, and the like) and laboratory animals (e.g., rats, mice, guinea pigs, and the like). The mammal treated in the methods described in the disclosure is preferably a mammal in which treatment, for example, of pain or depression is desired.

The term "treating," as used herein, includes any effect, for example, lessening, reducing, modulating, ameliorating, or eliminating, that results in the improvement of the condition, disease, disorder, and the like, including one or more symptoms thereof. Treating can be curing, improving, or at least partially ameliorating the disorder.

The term "disorder" refers to and is used interchangeably with, the terms "disease," "condition," or "illness," unless otherwise indicated.

The term "modulation," as used herein, refers to and includes antagonism (e.g., inhibition), agonism, partial antagonism, and/or partial agonism.

The phrases "pharmaceutically effective amount" and "therapeutically effective amount," as used herein, refer to the amount of a compound (e.g., a disclosed compound) that will elicit the biological or medical response of a tissue, system, animal or human that is being sought by the researcher, veterinarian, medical doctor or other clinician. The compounds described in the disclosure can be administered in therapeutically effective amounts to treat a disease. A therapeutically effective amount of a compound can be the quantity required to achieve a desired therapeutic and/or prophylactic effect, such as an amount which results in lessening of a symptom of a disease or disorder such as depression.

The phrase "pharmaceutically acceptable salt(s)," as used herein, refers to salt(s) of acidic or basic groups that can be present in compounds of the disclosure and/or used in the compositions of the disclosure. A pharmaceutically acceptable salt (e.g., acid or base) of a compound of the present disclosure, upon administration to a patient, is capable of providing a compound of this invention or an active metabolite or residue thereof.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds disclosed herein can exist in a solvated form as well as an unsolvated form with pharmaceutically acceptable solvents such as water, ethanol, and the like, and it is intended that the disclosure embrace both solvated and unsolvated forms. In some embodiments, the compound is amorphous. In certain embodiments, the compound is a single polymorph. In various embodiments, the compound is a mixture of polymorphs. In particular embodiments, the compound is in a crystalline form.

The term "prodrug," as used herein, refers to compounds that are transformed in vivo to yield a disclosed compound or a pharmaceutically acceptable salt, hydrate or solvate of the compound. The transformation can occur by various mechanisms (such as by esterase, amidase, phosphatase, oxidative and or reductive metabolism) in various locations (such as in the intestinal lumen or upon transit into the intestine, blood or liver). Prodrugs are well known in the art (see, e.g., Rautio, Kumpulainen, et al., Nature Reviews Drug Discovery 2008, 7, 255). For example, if a compound described herein or a pharmaceutically acceptable salt, hydrate or solvate of the compound contains a carboxylic acid functional group, a prodrug can be an ester formed by the replacement of the hydrogen atom of the carboxylic acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$) alkylcarbamoyl-($C_1$-$C_2$)alkyl, piperidino-($C_2$-$C_3$)alkyl, pyrrolidino-($C_2$-$C_3$)alkyl, or morpholino-($C_2$-$C_3$)alkyl.

Similarly, if a compound described herein contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a compound described herein incorporates an amine functional group, a prodrug can be formed, for example, by creation of an amide or carbamate, an N-acyloxyalkyl derivative, an (oxodioxolenyl) methyl derivative, an N-Mannich base, imine or enamine. In addition, a secondary amine can be metabolically cleaved to generate a bioactive primary amine, or a tertiary amine can metabolically cleaved to generate a bioactive primary or secondary amine See, for example, Simplício, et al., *Molecules* 2008, 13, 519 and references therein.

Unless defined otherwise, all technical and scientific terms used herein have the same meaning as commonly understood by one of ordinary skill in the art to which this disclosure pertains.

Throughout the description, where compositions and kits are described as having, including, or comprising specific components, or where processes and methods are described as having, including, or comprising specific steps, it is contemplated that, additionally, there are compositions and kits of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure(s). For example, it will be appreciated that all features described and depicted herein can be applicable to all aspects of the disclosure(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also include the specific quantitative value itself, unless specifically stated otherwise. As used herein, the term "about" refers to a ±10% variation from the nominal value unless otherwise indicated or inferred.

Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

Further, if a variable is not accompanied by a definition, then the variable is defined as found elsewhere in the disclosure unless understood to be different from the context. In addition, the definition of each variable and/or substituent, for example, $C_1$-$C_6$ alkyl, $R^2$, $R^b$, w and the like, when it occurs more than once in any structure or compound, can be independent of its definition elsewhere in the same structure or compound.

Definitions of the variables and/or substituents in formulae and/or compounds herein encompass multiple chemical groups. The present disclosure includes embodiments where, for example, i) the definition of a variable and/or substituent is a single chemical group selected from those chemical groups set forth herein, ii) the definition is a collection of two or more of the chemical groups selected from those set forth herein, and iii) the compound is defined by a combination of variables and/or substituents in which the variables and/or substituents are defined by (i) or (ii).

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

Compounds

Disclosed compounds include a compound having the formula:

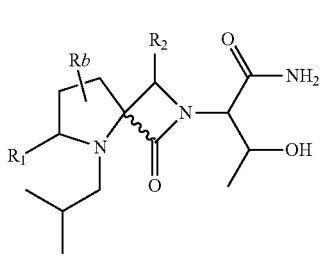

(I)

or a stereoisomer, an N-oxide, and/or a pharmaceutically acceptable salt thereof, where $R^b$ is selected from the group consisting of hydrogen, halogen, hydroxyl, cyano, and $C_1$-$C_6$ alkyl; $R^1$ is selected from the group consisting of hydrogen, halogen, and $C_1$-$C_6$ alkyl; and $R^2$ is selected from the group consisting of hydrogen, halogen, and $C_1$—C alkyl.

In some embodiments, $R^1$ is hydrogen. In certain embodiments, $R^1$ is $C_1$-$C_6$ alkyl, for example, methyl ($CH_3$).

In some embodiments, $R^2$ is hydrogen. In certain embodiments, $R^2$ is $C_1$-$C_6$ alkyl, for example, methyl ($CH_3$).

In some embodiments (including any of the embodiments described herein), $R^b$ is hydrogen. In some embodiments, $R^b$ is $C_1$-$C_6$ alkyl, for example, methyl ($CH_3$).

In various embodiments, a disclosed compound has the formula:

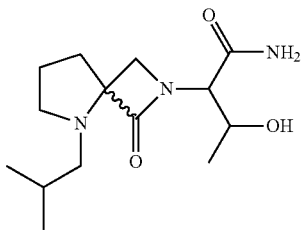 [SMILES: CC(C)CN1CCCC12CN(C(C(N)=O)C(C)O)C2=O]

or a stereoisomer, an N-oxide, and/or a pharmaceutically acceptable salt thereof.

In some embodiments, the compound is selected from the compounds delineated in the Examples.

In certain embodiments, a disclosed compound has the formula:

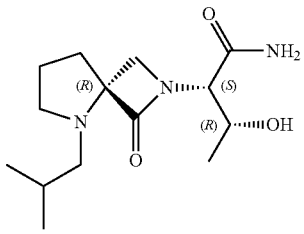

or an N-oxide and/or a pharmaceutically acceptable salt thereof.

In certain embodiments, a disclosed compound has the formula:

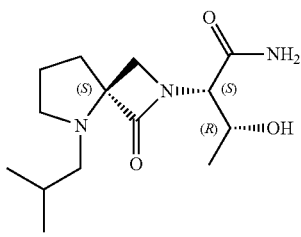

or an N-oxide and/or a pharmaceutically acceptable salt thereof.

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

The compounds described herein, in some embodiments, bind to a specific NMDA receptor subtypes. For example, a disclosed compound may bind to one NMDA subtype and not another. In certain embodiments, a disclosed compound may bind to one, or more than one NMDA subtype, and/or e.g. may have substantially less (or substantial no) binding activity to certain other NMDA subtypes. For example, in some embodiments, a disclosed compound (e.g., compound A) binds to NR2A with substantially no binding to NR2D. In some embodiments, a disclosed compound (e.g., compound B) binds to NR2B and NR2D with substantially lower binding to NR2A and NR2C.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or greater than the activity of existing NMDA receptor glycine site partial agonists.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=$(TD_{50}):(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects, formulations and compositions comprising a disclosed compound and optionally a pharmaceutically acceptable excipient are provided. In some embodiments, a formulation includes a racemic mixture of one or more of the disclosed compounds.

Formulations can be prepared in any of a variety of forms for use. By way of example, and not limitation, the compounds can be prepared in a formulation suitable for oral administration, subcutaneous injection, or other methods for administering an active agent to a patient, who may be in need thereof, as are known in the pharmaceutical arts. For example, pharmaceutical compositions of the disclosure can be suitable for delivery to the eye. Related methods can include administering a pharmaceutically effective amount of a disclosed compound or a pharmaceutical composition including a disclosed compound to a patient in need thereof, for example, to an eye of the patient, where administering can be topically, subconjunctivally, subtenonly, intravitreally, retrobulbarly, peribulbarly, intracomerally, and/or systemically.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect, a compound may be formulated with one or more additional compounds that enhance the solubility of the compound.

Methods

Methods for treating a condition in a patient in need thereof by administering a therapeutically effective amount or dose of a compound described herein are provided. In some embodiments, the condition can be a mental condition. For example, a mental illness can be treated. In another aspect, a nervous system condition can be treated. For example, a condition that affects the central nervous system, the peripheral nervous system, and/or the eye can be treated. In some embodiments, neurodegenerative diseases can be treated.

In some embodiments, the methods include administering a compound to treat patients suffering from autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder (OCD), phobia, post-traumatic stress syndrome, a behavior disorder, an impulse control disorder, a substance abuse disorder (e.g., a withdrawal symptom, opiate addiction, nicotine addiction, and ethanol addition), a sleep disorder, a memory disorder (e.g., a deficit, loss, or reduced ability to make new memories), a learning disorder, urinary incontinence, multiple system atrophy, progressive supra-nuclear palsy, Friedrich's ataxia, Down's syndrome, fragilexsyndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, infantile spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic pain.

In some embodiments, methods of treating a memory disorder associated with aging, schizophrenia, special learning disorders, seizures, post-stroke convulsions, brain ischemia, hypoglycemia, cardiac arrest, epilepsy, Lewy body dementia, migraine, AIDS dementia, Huntington's chorea, Parkinson's disease, early stage Alzheimer's disease, and Alzheimer's disease are provided.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions described herein. Psychotic disorders such as schizoaffective disorders, delusional disorders, brief psychotic disorders, shared psychotic disorders, and psychotic disorders with delusions or hallucinations may also be treated using the compositions described herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the patient may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only. Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis. In certain embodiments, methods for treating delusions (e.g., "non-bizarre") that may be present in, for example, delusional disorder are provided.

In various embodiments, methods for treating social withdrawal in conditions including, but not limited to, social anxiety disorder, avoidant personality disorder, and schizotypal personality disorder are provided.

In some embodiments, the disclosure provides methods for treating a neurodevelopmental disorder related to synaptic dysfunction in a patient in need thereof, where the methods generally include administering to the patient a therapeutically effective amount of a disclosed compound, or a pharmaceutical composition including a disclosed compound. In certain embodiments, the neurodevelopmental disorder related to synaptic dysfunction can be Rett syndrome also known as cerebroatrophic hyperammonemia, MECP2 duplication syndrome (e.g., a MECP2 disorder), CDKL5 syndrome, fragilexsyndrome (e.g., a FMR1 disorder), tuberous sclerosis (e.g., a TSC1 disorder and/or a TSC2 disorder), neurofibromatosis (e.g., a NF1 disorder), Angelman syndrome (e.g., a UBE3A disorder), the PTEN hamartoma tumor syndrome, Phelan-McDermid syndrome (e.g., a SHANK3 disorder), or infantile spasms. In particular embodiments, the neurodevelopmental disorder can be caused by mutations in the neuroligin (e.g., a NLGN3 disorder and/or a NLGN2 disorder) and/or the neurexin (e.g., a NRXN1 disorder).

In some embodiments, methods are provided for treating neuropathic pain. The neuropathic pain may be acute or chronic. In some cases, the neuropathic pain may be associated with a condition such as herpes, HIV, traumatic nerve injury, stroke, post-ischemia, chronic back pain, post-herpetic neuralgia, fibromyalgia, reflex sympathetic dystrophy, complex regional pain syndrome, spinal cord injury, sciatica, phantom limb pain, diabetic neuropathy such as diabetic peripheral neuropathy (DPN), and cancer chemotherapeutic-induced neuropathic pain. Methods for enhancing pain relief and for providing analgesia to a patient are also provided.

In various embodiments, methods of the disclosure include a method of treating autism and/or an autism spectrum disorder in a patient need thereof, comprising administering an effective amount of a disclosed compound to the patient. In some embodiments, a method for reducing the symptoms of autism in a patient in need thereof is provided, where the method includes administering an effective amount of a disclosed compound to the patient. For example, upon administration, the compound may decrease the incidence of one or more symptoms of autism such as eye contact avoidance, failure to socialize, attention deficit, poor mood, hyperactivity, abnormal sound sensitivity, inappropriate speech, disrupted sleep, and perseveration. Such decreased incidence may be measured relative to the incidence in the untreated individual or an untreated individual(s).

Also provided herein is a method of modulating an autism target gene expression in a cell comprising contacting a cell with an effective amount of a compound described herein. The autism gene expression may be for example, selected from ABAT, APOE, CHRNA4, GABRA5, GFAP, GRIN2A, PDYN, and PENK. In certain embodiments, a method of modulating synaptic plasticity in a patient suffering from a synaptic plasticity related disorder is provided, comprising administering to the patient an effective amount of a compound.

In some embodiments, a method of treating Alzheimer's disease, or e.g., treatment of memory loss that e.g., accompanies early stage Alzheimer's disease, in a patient in need thereof is provided, comprising administering a compound. Also provided herein is a method of modulating an Alzheimer's amyloid protein (e.g., beta amyloid peptide, e.g. the isoform $A\beta_{1-42}$), in-vitro or in-vivo (e.g. in a cell) comprising contacting the protein with an effective amount of a compound is disclosed. For example, in some embodiments, a compound may block the ability of such amyloid protein to inhibit long-term potentiation in hippocampal slices as well as apoptotic neuronal cell death. In some embodiments, a disclosed compound can provide neuroprotective properties to a Alzheimer's patient in need thereof, for example, a therapeutic effect on later stage Alzheimer's-associated neuronal cell death.

In certain embodiments, the disclosed methods include treating a psychosis or a pseudobulbar affect ("PBA") that is induced by another condition such as a stroke, amyotrophic lateral sclerosis (ALS or Lou Gehrig's disease), multiple sclerosis, traumatic brain injury, Alzheimer's disease, dementia, and/or Parkinson's disease. Such methods, as with other methods of the disclosure, include administration of a pharmaceutically effective amount of a disclosed compound to a patient in need thereof.

In various embodiments, a method of treating depression comprising administering a compound described herein is provided. In some embodiments, the treatment may relieve depression or a symptom of depression without affecting behavior or motor coordination and without inducing or promoting seizure activity. Exemplary depression conditions that are expected to be treated according to this aspect include, but are not limited to, major depressive disorder, dysthymic disorder, psychotic depression, postpartum depression, premenstrual syndrome, premenstrual dysphoric disorder, seasonal affective disorder (SAD), bipolar disorder (or manic depressive disorder), mood disorder, and depressions caused by chronic medical conditions such as cancer or chronic pain, chemotherapy, chronic stress, and post-traumatic stress disorders. In addition, patients suffering from any form of depression often experience anxiety. Various symptoms associated with anxiety include fear, panic, heart palpitations, shortness of breath, fatigue, nausea, and headaches among others. Anxiety or any of the symptoms thereof may be treated by administering a compound as described herein.

Also provided herein are methods of treating a condition in treatment-resistant patients, e.g., patients suffering from a mental or central nervous system condition that does not, and/or has not, responded to adequate courses of at least one, or at least two, other compounds or therapeutics. For example, provided herein is a method of treating depression in a treatment resistant patient, comprising a) optionally identifying the patient as treatment resistant and b) administering an effective dose of a compound to said patient.

In some embodiments, a compound described herein may be used for acute care of a patient. For example, a compound can be administered to a patient to treat a particular episode (e.g., a severe episode) of a condition described herein.

Also included herein are combination therapies comprising a disclosed compound in combination with one or more other active agents. For example, a disclosed compound may be combined with one or more antidepressants, such as tricyclic antidepressants, MAO-I's, SSRI's, and double and triple uptake inhibitors and/or anxiolytic drugs. Exemplary drugs that may be used in combination with a compound include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In other examples, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. It should be understood that combinations of a compound and one or more of the above therapeutics may be used for treatment of any suitable condition and are not limited to use as antidepressants or antipsychotics.

EXAMPLES

The following examples are provided for illustrative purposes only, and are not intended to limit the scope of the disclosure.

The following abbreviations may be used herein and have the indicated definitions: Ac is acetyl (—C(O)CH$_3$), AIDS is acquired immune deficiency syndrome, Boc and BOC are tert-butoxycarbonyl, Boc$_2$O is di-tert-butyl dicarbonate, Bn is benzyl, BOM-Cl is benzyloxymethyl chloride, CAN is ceric ammonium nitrate, Cbz is carboxybenzyl, DCM is dichloromethane, DIAD is diisopropyl azodicarboxylate, DIPEA is N,N-diisopropylethylamine, DMAP is 4-dimethylaminopyridine, DMF is N,N-dimethylformamide, DMSO is dimethyl sulfoxide, EDC and EDCI are 1-ethyl-3-(3-dimethylaminopropyl)carbodiimide hydrochloride, ESI is electrospray ionization, EtOAc is ethyl acetate, Gly is glycine, h is hour, HATU is 2-(7-aza-1H-benzotriazole-1-yl)-1,1,3,3-tetramethyluronium hexafluorophosphate, HIV is human immunodeficiency virus, HOBt is hydroxybenzotriazole, HPLC is high performance liquid chromatography, LCMS is liquid chromatography/mass spectrometry, LDA is lithium diisopropylamide, LiHMDS is lithium hexamethyldisilazane, MTBE is methyl tert-butyl ether, NMDAR is N-methyl-d-aspartate receptor, NMP is N-methyl-2-pyrrolidone, NMR is nuclear magnetic resonance, Pd/C is palladium on carbon, PMB is para-methoxybenzyl, RT is room temperature (e.g., from about 20° C. to about 25° C.), TBS and TBDMS are tert-butyldimethylsilyl, TEA is triethylamine, TLC is thin layer chromatography, TFA is trifluoroacetic acid, THF is tetrahydrofuran, TMS is trimethylsilyl, TMSCN is trimethylsilyl cyanide, and TPP is triphenylphosphine.

Example 1—Synthesis of Compound a and Compound a Maleic Acid Salt

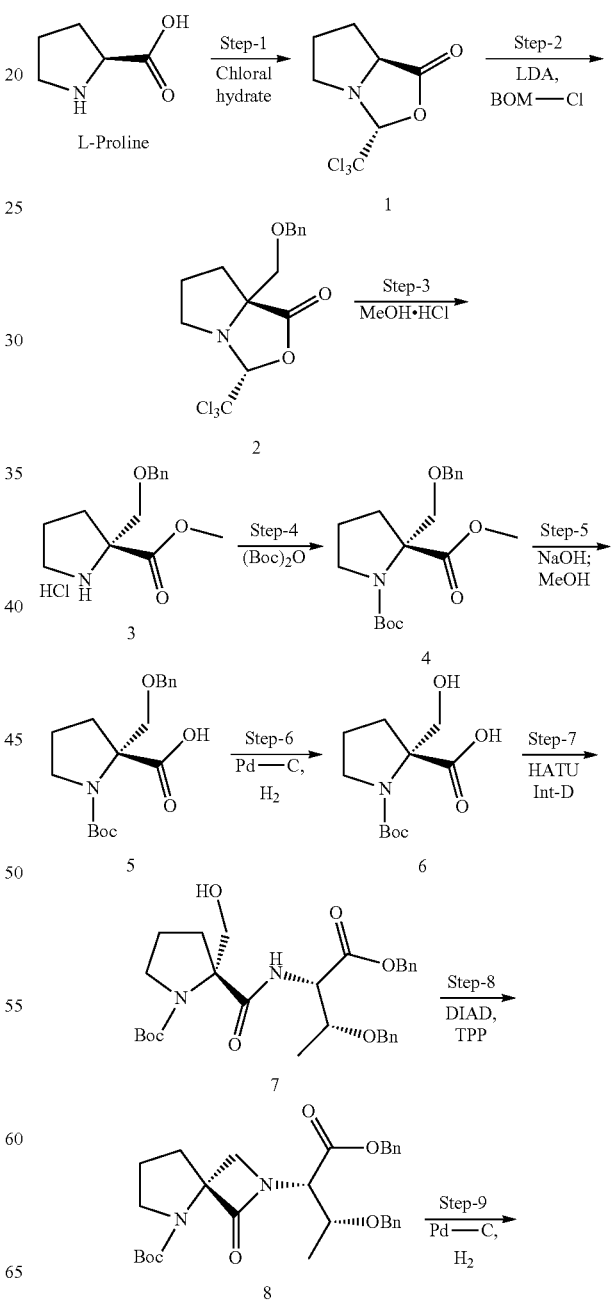

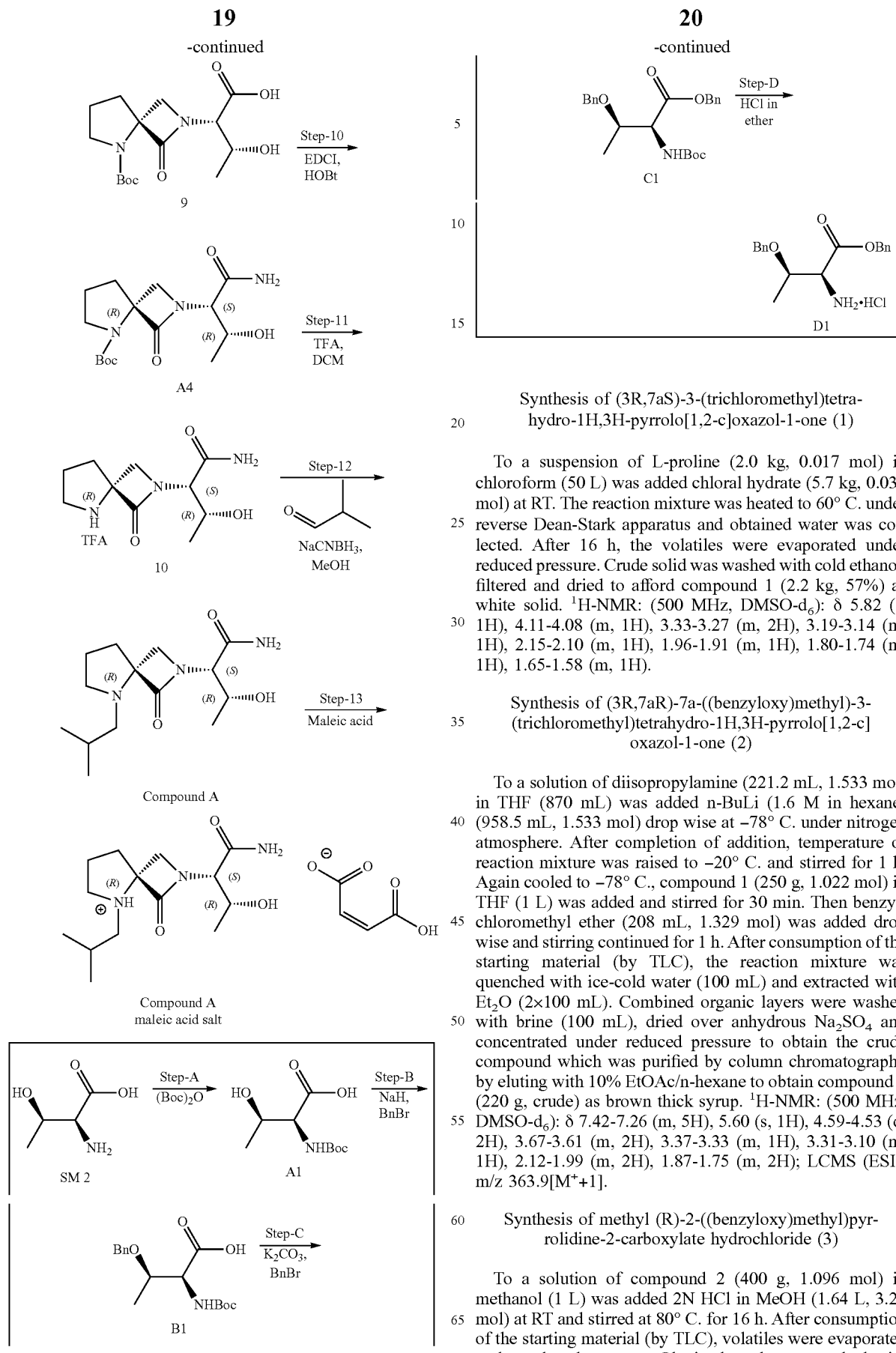

Synthesis of (3R,7aS)-3-(trichloromethyl)tetrahydro-1H,3H-pyrrolo[1,2-c]oxazol-1-one (1)

To a suspension of L-proline (2.0 kg, 0.017 mol) in chloroform (50 L) was added chloral hydrate (5.7 kg, 0.034 mol) at RT. The reaction mixture was heated to 60° C. under reverse Dean-Stark apparatus and obtained water was collected. After 16 h, the volatiles were evaporated under reduced pressure. Crude solid was washed with cold ethanol, filtered and dried to afford compound 1 (2.2 kg, 57%) as white solid. $^1$H-NMR: (500 MHz, DMSO-$d_6$): δ 5.82 (s, 1H), 4.11-4.08 (m, 1H), 3.33-3.27 (m, 2H), 3.19-3.14 (m, 1H), 2.15-2.10 (m, 1H), 1.96-1.91 (m, 1H), 1.80-1.74 (m, 1H), 1.65-1.58 (m, 1H).

Synthesis of (3R,7aR)-7a-((benzyloxy)methyl)-3-(trichloromethyl)tetrahydro-1H,3H-pyrrolo[1,2-c]oxazol-1-one (2)

To a solution of diisopropylamine (221.2 mL, 1.533 mol) in THF (870 mL) was added n-BuLi (1.6 M in hexane) (958.5 mL, 1.533 mol) drop wise at −78° C. under nitrogen atmosphere. After completion of addition, temperature of reaction mixture was raised to −20° C. and stirred for 1 h. Again cooled to −78° C., compound 1 (250 g, 1.022 mol) in THF (1 L) was added and stirred for 30 min. Then benzylchloromethyl ether (208 mL, 1.329 mol) was added drop wise and stirring continued for 1 h. After consumption of the starting material (by TLC), the reaction mixture was quenched with ice-cold water (100 mL) and extracted with Et$_2$O (2×100 mL). Combined organic layers were washed with brine (100 mL), dried over anhydrous Na$_2$SO$_4$ and concentrated under reduced pressure to obtain the crude compound which was purified by column chromatography by eluting with 10% EtOAc/n-hexane to obtain compound 2 (220 g, crude) as brown thick syrup. $^1$H-NMR: (500 MHz, DMSO-$d_6$): δ 7.42-7.26 (m, 5H), 5.60 (s, 1H), 4.59-4.53 (d, 2H), 3.67-3.61 (m, 2H), 3.37-3.33 (m, 1H), 3.31-3.10 (m, 1H), 2.12-1.99 (m, 2H), 1.87-1.75 (m, 2H); LCMS (ESI): m/z 363.9[M$^+$+1].

Synthesis of methyl (R)-2-((benzyloxy)methyl)pyrrolidine-2-carboxylate hydrochloride (3)

To a solution of compound 2 (400 g, 1.096 mol) in methanol (1 L) was added 2N HCl in MeOH (1.64 L, 3.29 mol) at RT and stirred at 80° C. for 16 h. After consumption of the starting material (by TLC), volatiles were evaporated under reduced pressure. Obtained crude was washed with hexanes (3×750 mL) and dried under reduced pressure to afford compound 3 (358 g, crude) as reddish thick syrup. $^1$H-NMR: (500 MHz, DMSO-$d_6$): δ 10.40 (br s, 1H), 7.40-7.21 (m, 5H), 4.64-4.50 (d, 2H), 4.49-4.3 (d, 2H), 3.76 (s, 3H), 3.33-3.22 (m, 2H), 2.22-2.15 (s, 1H), 2.02-1.9 (m, 2H), 1.95-1.83 (m, 1H).

Synthesis of 1-(tert-butyl) 2-methyl (R)-2-((benzyloxy)methyl)pyrrolidine-1,2-dicarboxylate (4)

To a stirred suspension of compound 3 (313 g, crude 1.096 mol) in DCM (2.19 L) was added Et$_3$N (458.4 mL, 3.288 mol) drop wise at 0° C. under nitrogen atmosphere and stirred for 10 min. Then Boc anhydride (358.4 g, 1.644 mol) was added drop wise at 0° C. The reaction mixture was brought to RT and stirred for 16 h. After consumption of the starting material (by TLC), the reaction was diluted with water (2×1 L) and extracted with CH$_2$Cl$_2$ (2×500 mL). The combined organic layer was washed with 10% citric acid (pH-7) and brine solution (1 L). The organic layer was dried over Na$_2$SO$_4$ and concentrated under reduced pressure to afford crude compound which was purified by column chromatography by eluting with 20% EtOAc/n-hexane to obtain compound 4 (215 g, 56%) as colourless thick syrup. $^1$H-NMR: (500 MHz, DMSO-$d_6$): δ 7.37-7.26 (m, 5H), 4.56-4.48 (m, 2H), 4.03-3.87 (dd, 1H), 3.69-3.67 (d, 1H), 3.62 (s, 3H), 3.53-3.47 (m, 1H), 3.33-3.30 (m, 1H), 2.27-2.20 (m, 1H), 2.03-1.89 (m, 2H), 1.88-1.79 (m, 1H), 1.46-1.24 (2s, 9H); LCMS (ESI): m/z 250.1 [(M$^+$+1)-Boc].

Synthesis of (R)-2-((benzyloxy)methyl)-1-(tert-butoxycarbonyl)pyrrolidine-2-carboxylic acid (5)

To a solution of compound 4 (215 g, 0.616 mol) in MeOH: THF: H$_2$O (3 L, 5:5:3) was added NaOH (73.9 g, 1.848 mol) and stirred at RT for 10 min. The reaction mixture was heated to 80° C. and stirred for 16 h. After consumption of the starting material (by TLC), reaction mixture was brought to RT, volatiles were evaporated. Crude material was diluted with water (1 L) and extracted with Et$_2$O (2×500 mL). The separated aqueous layer was acidified using 2 N HCl solutions (pH-3) and extracted with DCM (2×750 mL). Combined organic layers were washed with brine solution, dried over Na$_2$SO$_4$ and concentrated to afford compound 5 (170 g, 82.4%) as off white solid. $^1$H-NMR: (500 MHz, DMSO-$d_6$): δ 12.66 (br s, 1H), 7.36-7.26 (m, 5H), 4.54-4.47 (m, 2H), 4.05-3.90 (dd, 1H), 3.88-3.63 (d, 1H), 3.63-3.44 (m, 1H), 3.34-3.27 (m, 1H), 2.27-2.01 (m, 1H), 2.02-1.8 (m, 2H), 1.79-1.76 (m, 1H), 1.17-1.14 (2s, 9H); LCMS (ESI): m/z 235.1[(M$^+$+1)-Boc].

Synthesis of (R)-1-(tert-butoxycarbonyl)-2-(hydroxymethyl)pyrrolidine-2-carboxylic acid (6)

To a stirring solution of compound 5 (170 g, 0.507 mol) in CH$_3$OH (1 L) was added 50% wet 10% Pd—C(68 g) at RT and stirred for 16 h under H$_2$ atmosphere. After consumption of the starting material (by TLC), the reaction mixture was filtered through a pad of celite and the pad was washed with CH$_3$OH (1 L). Obtained filtrate was concentrated under reduced pressure to afford compound 6 (110 g, 88%) as white solid. $^1$H-NMR: (400 MHz, DMSO-$d_6$): δ 12.66 (br s, 1H), 3.96-3.83 (dd, 1H), 3.63-3.60 (m, 1H), 3.49-3.46 (m, 1H), 3.34-3.25 (m, 2H), 2.30-2.15 (m, 1H), 1.95-1.72 (m, 3H), 1.38-1.33 (2s, 9H); LCMS (ESI): m/z 244 [M$^+$–1]; Chiral HPLC: 95.88%.

Synthesis of tert-butyl (R)-2-(((2S,3R)-1,3-bis(benzyloxy)-1-oxobutan-2-yl)carbamoyl)-2-(hydroxymethyl)pyrrolidine-1-carboxylate (7)

To a stirring solution of compound 6 (110 g, 0.448 mol) in DCM (20 mL) cooled to 0° C. under N$_2$ atmosphere were added diisopropylethylamine (206 mL, 1.12 mol), Intermediate D1 (150 g, 0.448 mol) and HATU (204 g, 0.537 mol). The reaction mixture was brought to RT and stirred for 4 h. After consumption of the starting material (by TLC), the reaction mixture was diluted with DCM (1 L) and washed with water (2×500 mL), 10% citric acid solution (500 mL) and brine solution (500 mL). Organic layer was dried over anhydrous Na$_2$SO$_4$ and concentrated under reduced pressure to afford crude compound which was purified by column chromatography by eluting with 30% EtOAc/n-hexane to obtain compound 7 (143 g, 60%) as colourless thick syrup. $^1$H-NMR: (500 MHz, DMSO-$d_6$): δ 8.20-8.12 (d, 1H), 7.29-7.18 (m, 10H), 5.83-5.59 (m, 1H), 5.08 (s, 2H), 4.50-4.44 (m, 2H), 4.30-4.26 (m, 1H), 4.08-4.00 (m, 2H), 3.42-3.40 (m, 2H), 3.39-3.29 (m, 1H), 2.19-2.08 (m, 1H), 1.96-1.87 (m, 1H), 1.68-1.63 (m, 2H), 1.23-1.15 (2s, 9H), 1.14-1.13 (d, 3H); LCMS (m/z): 525.2 [M$^+$–1]; HPLC: 76.2%; Chiral HPLC: 69.47%.

Synthesis of tert-butyl (R)-2-((2S,3R)-1,3-bis(benzyloxy)-1-oxobutan-2-yl)-1-oxo-2,5-diazaspiro[3.4]octane-5-carboxylate (8)

To a solution of triphenylphosphine (161.4 g, 0.612 mol) in THF (430 mL) was added DIAD (123.8 g, 0.612 mol) drop wise at RT under nitrogen atmosphere and stirred for 15 minutes. To this, compound 7 (215 g, 0.408 mol) in THF (860 mL) solution was added drop wise and allowed to stir RT for 4 h. After consumption of the starting material (by TLC), volatiles were evaporated under reduced pressure. Obtained crude material was purified by silica gel column chromatography eluting with 20% EtOAc/hexane to afford compound 8 (180 g, mixture with DIAD by product) as yellow syrup. $^1$H-NMR: (400 MHz, DMSO-$d_6$): δ 7.31-7.18 (m, 10H), 5.18-5.10 (m, 2H), 4.61-4.54 (m, 2H), 4.27-4.18 (m, 2H), 3.78-3.77 (d, 1H), 3.45-3.43 (d, 1H), 3.35-3.31 (d, 1H), 3.27-3.23 (m, 1H), 2.03-1.98 (m, 2H), 1.78-1.76 (m, 2H), 1.39-1.31 (2s, 9H), 1.23-1.22 (d, 3H) (DIAD by product peaks were not captured); LCMS (ESI): m/z 509.4 [M$^+$+1].

Synthesis of (2S,3R)-2-((R)-5-(tert-butoxycarbonyl)-1-oxo-2,5-diazaspiro[3.4]octan-2-yl)-3-hydroxybutanoic acid (9)

A solution of compound 8 (85 g, 0.167 mol) in methanol (850 mL) was degassed under N$_2$ atmosphere. Then added 50% wet 10% Pd—C(40 g) at RT and stirred for 24 h under H$_2$ atmosphere. After consumption of the starting material (by TLC), the reaction mixture was filtered through a pad of celite and filtrate was concentrated under reduced pressure. Obtained crude solid was diluted with Et$_2$O (1 L) and vigorously stirred at RT for 1 h. Resultant solid material was filtered off and dried to afford compound 9 (75 g, 68%) as white solid. $^1$H-NMR: (400 MHz, DMSO-$d_6$): δ 12.86 (br s, 1H), 5.24 (br s 1H), 4.06-4.00 (m, 2H), 3.88-3.82 (m, 1H), 3.51-3.50 (m, 1H), 3.43-3.34 (m, 1H), 3.31-3.23 (m, 1H), 2.15-2.09 (m, 2H), 1.82-1.78 (m, 2H), 1.39-1.31 (2s, 9H), 1.10-1.08 (d, 3H); LCMS (m/z): 329.1 [M$^+$+1]; HPLC: 93.97%.

Synthesis of tert-butyl (R)-2-((2S,3R)-1-amino-3-hydroxy-1-oxobutan-2-yl)-1-oxo-2,5-diazaspiro[3.4]octane-5-carboxylate (A4)

To a stirring solution of compound 9 (150 g, 0.457 mol) in CH$_2$Cl$_2$ (2 L) at 0° C. were added diisopropylethylamine (176.85 g, 1.37 mol), NH$_4$Cl (48.8 g, 0.914 mol) and HATU (208.3 g 0.548 mol) under nitrogen atmosphere. The reaction mixture was brought to RT and stirred for 12 h. After consumption of the starting material (by TLC), the reaction mixture was diluted with water (2×750 mL) and extracted with CH$_2$Cl$_2$ (2×1 L). Combined organic layer was washed with 2N HCl solution and saturated sodium chloride solution (750 mL). Organic layer was dried over anhydrous Na$_2$SO$_4$ and concentrated under reduced pressure. Crude compound was purified by column chromatography pure compound was eluting with 3% MeOH/CH$_2$Cl$_2$. The obtained material was diluted with DCM (2 L) and washed with saturated citric acid (5×500 mL), saturated bicarbonate wash followed by brine wash and dried over Na$_2$SO$_4$. The material was triturated with the ether (2×500 mL) to afford compound A4 (80 g, 53%) as white solid. $^1$H-NMR: (400 MHz, D$_2$O): δ 4.36-4.21 (m, 2H), 4.03-3.98 (m, 1H), 3.76-3.67 (m, 1H), 3.56-3.37 (m, 2H), 2.32-2.23 (m, 2H), 1.97-1.93 (m, 2H), 1.49-1.47 (2s, 9H), 1.33-1.32 (d, 3H); LCMS (ESI): m/z 328.3 [M++1]; HPLC: 99.30%; Chiral HPLC: 98.97%; SOR (c=1, CH$_3$OH): −11.08.

Synthesis of (2S,3R)-3-hydroxy-2-((R)-1-oxo-2,5-diazaspiro[3.4]octan-2-yl)butanamide (10)

To a stirring solution of compound A4 (10 g, 0.030 mol) in CH$_2$Cl$_2$ (50 mL) was added TFA (24 mL, 0.3058 mol) at 0° C. under nitrogen atmosphere. The reaction mixture was brought to RT and stirred for 4 h. After consumption of the starting material (by TLC), volatiles were evaporated under reduced pressure. Obtained thick syrup material was washed with ether (2×100 mL) and hexane (1×100 mL) dried under vacuum to afford compound 10 (3.5 g, TFA salt) as thick syrup, which was taken to next step. Crude RM was preceded as such without purification. LCMS (ESI): m/z 228.1 [M$^+$+1].

Synthesis of (2S,3R)-3-hydroxy-2-((R)-5-isobutyl-1-oxo-2,5-diazaspiro[3.4]octan-2-yl)butanamide (Compound A)

To a stirring solution of compound 10 (10 g, TFA salt 0.028 mol) in methanol (50 mL) were added isobutyraldehyde (10 mL, 0.115 mmol) followed by AcOH (12 mL) at RT under nitrogen atmosphere and stirred for 10 minutes. Then, NaCNBH$_3$ (7.2 g, 11.5 mmol) was added portion wise and continued stirring for 16 h. After consumption of the starting material (by TLC), the reaction mixture was diluted with CH$_2$Cl$_2$ (10 mL) and concentrated under reduced pressure. Similar reaction was carried out with 5 g batch. Combined the both lots and the obtained crude material was purified by silica gel column chromatography eluting with 4% MeOH/DCM to afford mixture of (2S,3R)-3-hydroxy-2-((R)-5-isobutyl-1-oxo-2,5-diazaspiro[3.4]octan-2-yl)butanamide. The obtained mixture was further subjected to column chromatography, pure compound was eluted in 100% Ethyl acetate to afford (2S,3R)-3-hydroxy-2-((R)-5-isobutyl-1-oxo-2,5-diazaspiro[3.4]octan-2-yl)butanamide (8 g) as thick syrup. $^1$H-NMR: (500 MHz, CD$_3$OD): δ 4.16-4.12 (m, 1H), 4.09 (d, J=7.0 Hz, 1H), 3.60 (d, J=6.0 Hz, 1H), 3.54 (d, J=6.0 Hz, 1H), 2.97-2.93 (m, 1H), 2.75 (q, J=8.0 Hz, 1H), 2.47-2.45 (m, 2H), 2.22-2.18 (m, 1H), 2.16-2.10 (m, 1H), 1.92-1.83 (m, 2H), 1.76-1.73 (m, 1H), 1.24 (d, J=6.0 Hz, 3H), 0.92-0.89 (m, 6H); LCMS (ESI): m/z 284.1 [M$^+$+1]; HPLC: 97.65%; Chiral HPLC: 98.25%; SOR (c=1, CH$_3$OH): 1.6.

Synthesis of (4R)-2-((2S,3R)-1-amino-3-hydroxy-1-oxobutan-2-yl)-5-isobutyl-1-oxo-2,5-diazaspiro[3.4]oct-5-ium (Z)-3-carboxyacrylate (Compound A maleic acid salt)

To a solution of (2S,3R)-3-hydroxy-2-((R)-5-isobutyl-1-oxo-2,5-diazaspiro[3.4]octan-2-yl)butanamide (400 mg, 1.41 mmol) in H$_2$O (4 mL) was added maleic acid (148 mg, 1.27 mmol) at room temperature and stirred for 16 h. After consumption of the starting material (by TLC), water was removed under reduced pressure. Obtained crude material was triturated with pentane and hexane, dried under vacuum to afford (4R)-2-((2S,3R)-1-amino-3-hydroxy-1-oxobutan-2-yl)-5-isobutyl-1-oxo-2,5-diazaspiro[3.4]octan-5-ium (Z)-3-carboxyacrylate (530 mg, 94%) as a white solid. $^1$H NMR (500 MHz, CD$_3$OD) δ 6.29 (s, 2H), 4.21-4.12 (m, 2H), 3.91-3.85 (m, 1H), 3.83-3.79 (m, 1H), 3.61-3.51 (m, 1H), 3.29-3.19 (m, 1H), 3.04 (dd, J=9.0, 12.5 Hz, 1H), 2.90 (dd, J=5.8, 12.2 Hz, 1H), 2.52-2.43 (m, 1H), 2.40-2.31 (m, 1H), 2.25-1.97 (m, 3H), 1.28 (d, J=5.8 Hz, 3H), 1.04 (dd, J=6.4, 9.9 Hz, 6H); LCMS (ESI): m/z 284.3 [M$^+$+1-maleic acid]; HPLC: 96.83%; Melting point: 113.4° C.-117.5° C.

Preparation of Int-D

Synthesis of (tert-butoxycarbonyl)-L-threonine (A1)

To a solution of SM-2 (50 g, 0.420 mol) in 1,4-dioxane: water (500 mL, 1:1) was added NaHCO$_3$ (133 g, 1.255 mol) portion wise at RT and stirred for 15 min. Then Boc-anhydride (144 mL, 0.629 mol) was added drop wise to the reaction mixture and stirring was continued at RT for 16 h. After consumption of the starting material (by TLC), the reaction mixture was concentrated under reduced pressure and obtained residue was diluted with water (200 mL) and acidified by using 1N HCl (pH-2). The aqueous layer was extracted with EtOAc (2×300 mL). The combined organic layer was washed with brine (1×200 mL), dried over anhydrous Na$_2$SO$_4$, filtered and concentrated under reduced pressure to afford A1 (80 g, 87%) as colorless syrup. $^1$H-NMR: (500 MHz, DMSO-d$_6$): δ 12.5 (br s, 1H), 6.30 (d, J=8.5 Hz, 1H), 4.50 (br s, 1H), 4.05-4.02 (m, 1H), 3.88-3.86 (m, 1H), 1.39 (s, 9H), 1.08 (d, J=6.0 Hz, 3H);
LCMS (m/z): 218.1 [M$^+$−1]

Synthesis of O-benzyl-N-(tert-butoxycarbonyl)-L-threonine (B1)

To a stirring solution of compound A1 (80 g, 0.365 mol) in DMF (800 mL) was added 60% NaH (22 g, 0.913 mol) portion wise at −20° C. under N$_2$ atmosphere and stirred for 2 h. To this was added benzyl bromide (52 mL, 0.438 mol) drop wise and the reaction mixture was stirred at 0° C. for 4 h. After consumption of the starting material (by TLC), the reaction mixture was quenched with ice cold water and extracted with diethyl ether (2×500 mL). Aqueous layer acidified by using 1N HCl (pH~2). The aqueous layer was extracted with EtOAc (2 ×1 L). Separated organic layer washed with brine solution, dried over anhydrous Na$_2$SO$_4$ and concentrated under reduced pressure to afford compound B1 (84 g, crude) as thick syrup.

$^1$H-NMR: (500 MHz, DMSO-d$_6$): δ 12.64 (br s, 1H), 7.34-7.25 (m, 5H), 6.46 (d, J=8.5 Hz, 1H), 4.53 (d, J=11.5 Hz, 1H), 4.39 (d, J=12.0 Hz, 1H), 4.00-3.98 (m, 2H), 1.39 (s, 9H), 1.15 (d, J=6.0 Hz, 3H).

Synthesis of benzyl O-benzyl-N-(tert-butoxycarbonyl)-L-threoninate (C1)

To a stirring solution of compound B1 (78 g, 0.252 mol) in DMF (780 mL) was added K$_2$CO$_3$ (87 g, 0.631 mol) at RT under N$_2$ atmosphere and stirred for 30 min. To this benzyl bromide (45 mL, 0.378 mol) was added drop wise at RT and stirred for 16 h. The reaction mixture was quenched with water (2 L) and extracted with diethyl ether (2×1 L). The separated organic layer was washed with brine, dried over anhydrous Na$_2$SO$_4$ and concentrated under reduced pressure. The crude material was purified by silica gel column chromatography eluting with 10% EtOAc/n-hexane to afford compound C1 (68 g, 68%) as yellow syrup. $^1$H-NMR: (500 MHz, DMSO-d$_6$): δ 7.37-7.18 (m, 10H), 6.81 (d, J=9.0 Hz, 1H), 5.08 (s, 2H), 4.49 (d, J=12.0 Hz, 1H), 4.32 (d, J=12.0 Hz, 1H), 4.25-4.22 (m, 1H), 4.01-3.98 (m, 1H), 1.38 (s, 9H), 1.15 (d, J=6.0 Hz, 3H); Mass (ESI): m/z 399.4 [M+].

Synthesis of benzyl O-benzyl-L-threoninate hydrochloride (D1)

To a solution of compound C1 (68 g, 0.170 mol) in diethyl ether (500 mL) was added 4N HCl in 1,4-dioxane (130 mL, 0.511 mol) and stirred at RT for 16 h. After consumption of the starting material (by TLC), the reaction mixture was concentrated under reduced pressure. The crude material was dissolved in diethylether (1 L) and vigorously stirred at RT for 1 h. Obtained solid was filtered off and dried under reduced pressure to afford compound D1 (50 g, 87%) as white solid (HCl salt). $^1$H-NMR: (400 MHz, DMSO-d$_6$): δ 8.59 (s, 2H), 7.50-7.25 (m, 10H), 5.23 (d, J=12.5 Hz, 1H), 5.16 (d, J=12.5 Hz, 1H), 4.54 (d, J=12.0 Hz, 1H), 4.36 (d, J=12.0 Hz, 1H), 4.12-4.09 (m, 1H), 4.09-3.99 (m, 1H), 1.29 (d, J=6.5 Hz, 3H); Mass (ESI): m/z 336.4 [M$^+$+1].

Example 2—Synthesis of Compound B and Compound B Maleic Acid Salt

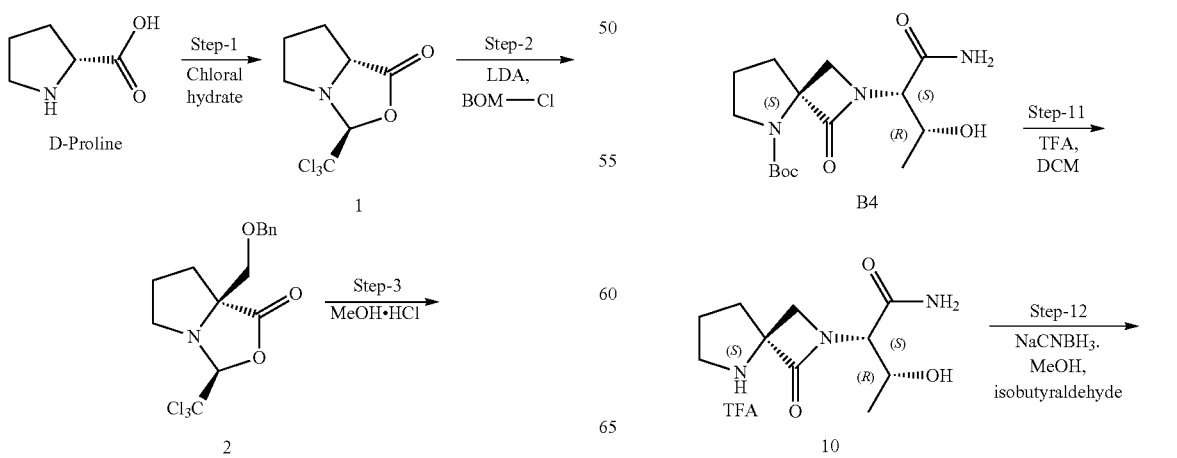

-continued

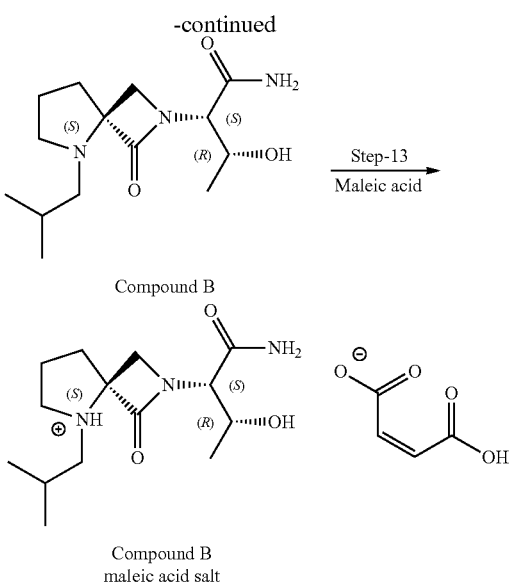

Compound B

Compound B maleic acid salt

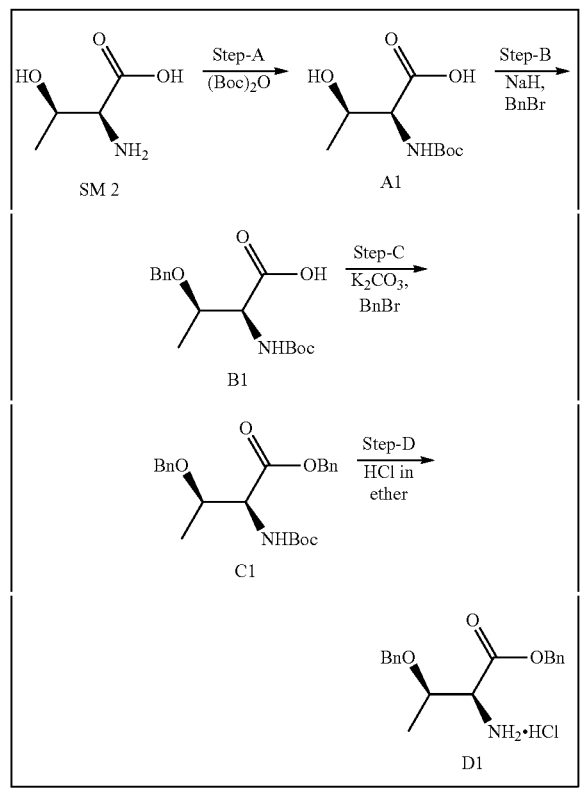

Synthesis of (3S,7aR)-3-(trichloromethyl)tetra-hydro-1H,3H-pyrrolo[1,2-c]oxazol-1-one (1)

To a suspension of D-proline (3 kg, 26.057 mol) in chloroform (60 L) was added chloral hydrate (8.62 kg, 52.115 mol) at RT. The reaction mixture was heated to 80° C. under reverse Dean-Stark apparatus and obtained water was collected. After being stirred for 24 h, reaction mixture was cooled to room temperature and added brine solution (25 L). Reaction mixture was stirred for 30 minutes and allowed to settle for 30 minutes. Separated organic layer was dried over Na$_2$SO$_4$ and concentrated under reduced pressure to afford volatiles were evaporated under reduced pressure.

Crude solid obtained was made slurry with cold ethanol (5 L), filtered and dried to afford compound 1 (4.7 kg, 74%) as an off white solid. $^1$H-NMR: (500 MHz, DMSO-d$_6$): δ 5.82 (s, 1H), 4.11-4.09 (m, 1H), 3.33-3.28 (m, 1H), 3.19-3.14 (m, 1H), 2.17-2.10 (m, 1H), 1.97-1.91 (m, 1H), 1.80-1.74 (m, 1H), 1.65-1.58 (m, 1H).

Synthesis of (3S,7aS)-7a-((benzyloxy)methyl)-3-(trichloromethyl)tetrahydro-1H,3H-pyrrolo[1,2-c]oxazol-1-one (2)

To a solution of diisopropylamine (442 mL, 3.067 mol) in THF (1 L) was added n-BuLi (1.6M in hexane) (1.91 L, 3.067 mol) drop wise at −78° C. under nitrogen atmosphere. After completion of addition, temperature of reaction mixture was raised to −20° C. and stirred for 45 minutes. Again cooled to −78° C., compound 1 (500 g, 2.044 mol) in THF (2 L) was added drop wise and stirred for 45 minutes. Then benzylchloromethyl ether (425 mL, 3.067 mol) was added drop wise and stirring continued for 2 h. After consumption of the starting material (by TLC), the reaction mixture was quenched with ice-cold water (2 L) and extracted with Et$_2$O (2×1 L). Combined organic layers were washed with brine (3 L), dried over Na$_2$SO$_4$ and concentrated under reduced pressure to afford crude compound which was purified by column chromatography by eluting with 10% EtOAc/n-hexane to obtain compound 2 (425 g, 57%) as yellow liquid. $^1$H-NMR: (500 MHz, DMSO-d$_6$): δ 7.35-7.26 (m, 5H), 5.60 (s, 1H), 4.59-4.53 (d, 2H), 3.67-3.62 (m, 2H), 3.71-3.31 (m, 1H), 3.16-3.11 (m, 1H), 2.12-1.99 (m, 2H), 1.86-1.72 (m, 2H); LCMS (ESI): m/z 363.8 [M$^+$−1].

Synthesis of methyl (S)-2-((benzyloxy)methyl)pyrrolidine-2-carboxylate hydrochloride (3)

To a solution of compound 2 (1 kg, 2.742 mol) in methanol (2 L) was added 2N HCl in methanol (4.1 L, 8.227 mol) at RT and stirred for 30 min. The reaction mixture was stirred at 60° C. for 16 h. After consumption of the starting material (by TLC), volatiles were evaporated under reduced pressure. Obtained crude syrup was diluted with DM water (3 L) and washed with EtOAc (2×1 L). Aqueous layer pH (8-9) was adjusted with NaHCO3 solution. Aqueous layer was extracted with 5% MeOH/DCM (2×2 L). Combined organic layer washed with brine solution, dried over Na$_2$SO$_4$ and concentrated under reduced pressure to afford compound 3 (600 g, 88%) as brown syrup. Another 1 kg batch was repeated and obtained 600 g of compound 3. $^1$H-NMR: (500 MHz, DMSO-d$_6$): δ 10.54 (br s, 1H), 9.44 (br s, 1H), 7.40-7.30 (m, 5H), 4.68-4.62 (d, 1H), 4.51-4.46 (d, 1H), 4.00-3.90 (m, 2H), 3.76 (s, 3H), 3.33-3.16 (m, 2H), 2.20-2.14 (s, 1H), 2.01-1.85 (m, 3H).

Synthesis of 1-(tert-butyl) 2-methyl (S)-2-((benzyloxy)methyl)pyrrolidine-1,2-dicarboxylate (4)

To a stirred suspension of compound 3 (1.2 kg, 4.819 mol) in DCM (6 L) was added Et$_3$N (1.35 L, 9.638 mol) drop wise at 0° C. under nitrogen atmosphere and stirred for 20 min. Then added Boc-anhydride (1.65 L, 7.228 mol) drop wise at 0° C. The reaction mixture was brought to RT and stirred for 8 h. After consumption of the starting material (by TLC), the reaction was diluted with DM water (3 L) and extracted with DCM (2 L). Combined organic layer was washed with 10% citric acid (2 L) solution and brine solution (2 L). Organic layer was dried over Na$_2$SO$_4$ and concentrated under reduced pressure to afford compound 4 (2 kg, crude) as brown syrup. $^1$H-NMR: (500 MHz, DMSO-d$_6$): δ 7.37-7.28 (m, 5H), 4.57-4.50 (m, 2H), 4.03-3.88 (dd, 1H), 3.71-3.69 (d, 1H), 3.63 (s, 3H), 3.52-3.47 (m, 1H), 3.36-3.31 (m, 1H), 2.32-2.23 (m, 1H), 2.05-1.88 (m, 2H), 1.82-1.77 (m, 1H), 1.38-1.26 (s, 9H); LCMS (ESI): m/z 350.2 [(M$^+$+1)].

Synthesis of (S)-2-((benzyloxy)methyl)-1-(tert-butoxycarbonyl)pyrrolidine-2-carboxylic acid (5)

To a solution of compound 4 (1 kg, 2.865 mol) in MeOH:THF (3 L, 1:1) was added NaOH (343.84 g, 8.595 mol) in H$_2$O (1.5 L) at RT stirred at 70° C. for 6 h. After consumption of the starting material (by TLC), reaction mixture was brought to RT, volatiles were evaporated under reduced pressure. Crude material was diluted with water (5 L) and extracted with EtOAc (2×2 L). The separated aqueous layer was acidified using 6N HCl solution (pH~2) and extracted with DCM (3×2 L). Combined organic layers were washed with brine solution, dried over Na$_2$SO$_4$ and concentrated to afford compound 5 (550 g, 58%) as brown syrup. Another 1 kg batch was repeated and obtained 550 g of compound 5. $^1$H-NMR: (500 MHz, DMSO-d$_6$): δ 12.68 (br s, 1H), 7.36-7.28 (m, 5H), 4.56-4.49 (m, 2H), 4.07-3.90 (dd, 1H), 3.66-3.64 (d, 1H), 3.50-3.44 (m, 1H), 2.29-2.20 (m, 1H), 2.03-1.75 (m, 3H), 1.39-1.28 (2s, 9H). LCMS (ESI): m/z 236.0 [M$^+$+1-Boc]; HPLC: 76.79%; Chiral HPLC: 96.26%

Synthesis of (S)-1-(tert-butoxycarbonyl)-2-(hydroxymethyl)pyrrolidine-2-carboxylic acid (6)

To a stirring solution of compound 5 (1.1 kg, 32.835 mol) in methanol (10 L) was added 50% wet 10% Pd—C(500 g) at RT and stirred for 8 h under H$_2$ atmosphere (3 kg). After consumption of the starting material (by TLC), the reaction mixture was filtered through a pad of celite and the pad was washed with methanol (50 mL). Obtained filtrate was concentrated under reduced pressure to obtain crude which was triturated with Et$_2$O to afford compound 6 (650 g, 81%) as an off white solid. $^1$H-NMR: (500 MHz, DMSO-d$_6$): δ 3.92-3.80 (dd, 1H), 3.64-3.61 (m, 1H), 3.49-3.34 (m, 1H), 3.32-3.26 (m, 1H), 2.29-2.16 (m, 1H), 1.95-1.71 (m, 3H), 1.38-1.33 (s, 9H); LCMS (ESI): m/z 243.8 [M$^+$−1].

Synthesis of tert-butyl (S)-2-(((2S,3R)-1,3-bis(benzyloxy)-1-oxobutan-2-yl)carbamoyl)-2-(hydroxymethyl)pyrrolidine-1-carboxylate (7)

To a solution of compound 6 (450 g, 0.836 mol) in DCM (4.5 L) was added N,N-diisopropylethylamine (846 mL, 4.591 mol) 0-5° C. under nitrogen atmosphere. After stirred for 10 minutes, Intermediate D1 (615 g, 1.836 mol) was added. After stirred for 10 minutes, HATU (701 g, 2.204 mol) was added. The reaction mixture was brought to RT and stirred for 6 h. After consumption of the starting material (by TLC), the reaction mixture was diluted with DCM (1 L) and washed with water (2×2 L), 10% citric acid solution (2 L) and brine solution (2 L). Organic layer was dried over anhydrous Na$_2$SO$_4$ and concentrated under reduced pressure to afford crude compound which was purified by column chromatography by eluting with 40% EtOAc/n-hexane to obtain compound 7, which was dissolved in Et$_2$O (1.5 L) and stirred for 1 h. Obtained precipitate was filter and dried under vacuum to afford compound 7 (630 g, 65%) as white solid. $^1$H-NMR: (400 MHz, DMSO-d$_6$): δ 7.91-7.89 (d, 0.5H), 7.53-7.51 (d, 0.5H), 7.32-7.19 (m, 10H), 5.64 (br s, 1H), 5.16-5.04 (m, 2H), 4.62-4.49 (m, 2H), 4.31-4.28 (m, 1H), 4.09-4.02 (m, 1.5H), 3.87 (br s, 1H), 3.57-3.56 (m, 0.5H), 3.43-3.37 (m, 1H), 3.29-3.25 (m, 1H), 2.32-2.14 (m, 1H), 1.98-1.90 (m, 1H), 1.75-1.69 (m, 2H), 1.33-1.26 (2s, 9H), 1.14-1.12 (d, 3H); LCMS (m/z): 527.6 [M++1]; HPLC: 96.60%.

Synthesis of tert-butyl (S)-2-((2S,3R)-1,3-bis(benzyloxy)-1-oxobutan-2-yl)-1-oxo-2,5-diazaspiro[3.4]octane-5-carboxylate (8)

To a solution of triphenylphosphine (295 g, 1.125 mol) in THF (846 mL) was added DIAD (227 g, 1.125 mol) drop wise at RT under nitrogen atmosphere and stirred for 30 minutes. Reaction mixture was cooled to 15° C., compound 7 (423 g, 0.804 mol) in THF (1.2 L) solution was added drop wise and allowed to stir RT for 4 h. Obtained crude material was washed with hexane followed by stirring with 50% Et$_2$O/hexane for 30 minutes. Formed precipitate was filtered off and the filtrate was concentrated under reduced pressure. Obtained crude was purified by silica gel column chromatography eluting with 40% EtOAc/hexane to afford compound 8 (425 g, crude) as brown syrup. $^1$H-NMR: (400 MHz, DMSO-d$_6$): δ 7.38-7.21 (m, 10H), 5.17-5.10 (m, 2H), 4.56-4.50 (m, 2H), 4.31-4.28 (d, 1H), 4.06-3.99 (m, 2H), 3.89-3.88 (d, 0.5H), 3.48-3.47 (d, 0.5H), 3.36-3.34 (m, 1H), 3.25-3.19 (m, 1H), 2.10-2.02 (m, 2H), 1.79-1.77 (m, 2H), 1.40-1.25 (s, 9H), 1.15-1.12 (d, 3H). LCMS (ESI): m/z 509.4 [M$^+$+1]; HPLC: 92.31%; Chiral HPLC: 86.47%.

Synthesis of (2S,3R)-2-((S)-5-(tert-butoxycarbonyl)-1-oxo-2,5-diazaspiro[3.4]octan-2-yl)-3-hydroxybutanoic acid (9)

A solution of compound 8 (283 g, 0.557 mol) in methanol (1.2 L) was degassed under N$_2$ atmosphere. Then added 50% wet 10% Pd—C(140 g) at RT and stirred for 24 h under H$_2$ atmosphere. After consumption of the starting material (by TLC), the reaction mixture was filtered through a pad of celite and filtrate was concentrated under reduced pressure. Obtained crude solid was diluted with Et$_2$O (500 mL) and vigorously stirred at 0° C. for 1 h. Resultant solid material was filtered off and dried to afford compound 9 (140 g, 76%) as white solid. $^1$H-NMR: (500 MHz, DMSO-d$_6$): δ 12.86 (br s, 1H), 5.24 (br s 1H), 4.06-4.00 (m, 2H), 3.88-3.82 (m, 1H), 3.51-3.50 (m, 1H), 3.43-3.34 (m, 1H), 3.31-3.23 (m, 1H), 2.15-2.09 (m, 2H), 1.82-1.78 (m, 2H), 1.39-1.31 (2s, 9H), 1.10-1.08 (d, 3H); LCMS (m/z): 327.1 [M$^+$−1]; HPLC: 95.44%; Chiral HPLC: 100.00%.

Synthesis of tert-butyl (S)-2-((2S,3R)-1-amino-3-hydroxy-1-oxobutan-2-yl)-1-oxo-2,5-diazaspiro[3.4]octane-5-carboxylate (B4)

To a stirring solution of compound 9 (420 g, 1.28 mol) in CH$_2$Cl$_2$ (4.2 L) were added HATU (584 g, 1.536 mol), NH$_4$Cl (137 g, 2.56 mol) and diisopropylethylamine (708 mL, 3.841 mol) at 0° C. under nitrogen atmosphere. The reaction mixture was brought to RT and stirred for 8 h. After consumption of the starting material (by TLC), the reaction mixture was partied between water (2 L) and CH$_2$Cl$_2$ (2 L) and stirred for 15 minutes. Organic layer was separated, washed with 2N HCl solution (2×1 L) and saturated NaHCO$_3$ solution (2 L) and brine solution (2 L). Organic layer was dried over anhydrous Na$_2$SO$_4$ and concentrated under reduced pressure. Obtained crude was purified by silica gel column chromatography eluting with 5% MeOH/CH$_2$Cl$_2$ to afford compound B4 (320 g, mixture) as off white solid. Mixture compound B4 (87 g) was dissolved in DCM and re-precipitated with Et₂O under vigorous stirring at RT for 1 h. Product was filter and dried under vacuum to obtain compound B4 (82 g) as white solid. ¹H-NMR: (400 MHz, D₂O): δ 4.53-4.10 (m, 2H), 4.08-3.96 (m, 1H), 3.80-3.72 (m, 1H), 3.60-3.39 (m, 2H), 2.53-2.31 (m, 2H), 2.02-1.93 (m, 2H), 1.51-1.45 (s, 9H), 1.31-1.29 (d, 3H); LCMS (ESI): m/z 326.1 [M⁺−1]; HPLC: 99.66%; Chiral HPLC: 99.76%; SOR (c=1, MeOH): −49.61.

Synthesis of (2S,3R)-3-hydroxy-2-((S)-1-oxo-2,5-diazaspiro[3.4]octan-2-yl)butanamide (10)

To a stirring solution of compound B4 (10 g, 0.031 mol) in CH₂Cl₂ (40 mL) was added TFA (23 mL, 0.305 mol) at 0° C. under nitrogen atmosphere. The reaction mixture was brought to RT and stirred for 3 h. After consumption of the starting material (by TLC), volatiles were evaporated under reduced pressure. Obtained thick syrup material was washed with ether (2×50 mL) and dried under vacuum to afford compound 10 (10 g, TFA salt, crude) as thick syrup, which was taken to next step. ¹H-NMR: (400 MHz, D₂O): δ 4.38-4.10 (m, 2H), 4.11-3.94 (m, 2H), 3.56-3.44 (m, 2H), 2.52-2.38 (m, 2H), 2.24-2.16 (m, 2H), 1.39-1.27 (d, 3H); LCMS (ESI): m/z 228.2 [M⁺+1].

Synthesis of (2S,3R)-3-hydroxy-2-((S)-5-isobutyl-1-oxo-2,5-diazaspiro[3.4]octan-2-yl)butanamide (Compound B)

To a stirring solution of crude compound 10 (10 g, TFA salt, 0.029 mol) in methanol (50 mL) were added isobutyraldehyde (6.5 mL, 0.073 mol) followed by AcOH (2.5 mL) at RT under nitrogen atmosphere and stirred for 10 minutes. Then, NaCNBH₃ (5.4 g, 0.087 mol) was added portion wise and continued stirring for 16 h. Consumption of the starting material (by TLC) did not complete. Again, isobutyraldehyde (3.2 mL, 0.036 mol) and AcOH (1 mL) were added and continued stirring for 2 h. After consumption of the starting material (by TLC), reaction mixture was diluted with CH₂Cl₂ (20 mL) and concentrated under reduced pressure. Obtained crude material was purified by silica gel column chromatography eluting with 4% MeOH/DCM to afford (2S,3R)-3-hydroxy-2-((S)-5-isobutyl-1-oxo-2,5-diazaspiro[3.4]octan-2-yl)butanamide (6 g) as thick syrup. ¹H-NMR: (500 MHz, CD₃OD): δ 4.10-4.07 (m, 2H), 3.63 (d, J=5.5 Hz, 1H), 3.49 (d, J=6.0 Hz, 1H), 2.97-2.93 (m, 1H), 2.74 (q, J=8.0 Hz, 1H), 2.41-2.34 (m, 2H), 2.26-2.20 (m, 1H), 2.17-2.11 (m, 1H), 1.94-1.81 (m, 2H), 1.73-1.69 (m, 1H), 1.21 (d, J=6.0 Hz, 3H), 0.91-0.89 (m, 6H); LCMS (ESI): m/z 284.1 [M⁺+1]; HPLC: 99.53%; Chiral HPLC: 100.00%; SOR (c=0.5, MeOH): −60.25.

Synthesis of (4S)-2-((2S,3R)-1-amino-3-hydroxy-1-oxobutan-2-yl)-5-isobutyl-1-oxo-2,5-diazaspiro[3.4]octan-5-ium (Z)-3-carboxyacrylate (Compound B maleic acid salt)

To a solution of (2S,3R)-3-hydroxy-2-((S)-5-isobutyl-1-oxo-2,5-diazaspiro[3.4]octan-2-yl)butanamide (180 mg, 0.636 mmol) in H₂O (2 mL) was added maleic acid (59 mg, 0.508 mmol) at room temperature and stirred for 16 h. After consumption of the starting material (by TLC), water was removed under reduced pressure. Obtained crude material was triturated with pentane and hexane, dried under vacuum to afford (4S)-2-((2S,3R)-1-amino-3-hydroxy-1-oxobutan-2-yl)-5-isobutyl-1-oxo-2,5-diazaspiro[3.4]octan-5-ium (Z)-3-carboxyacrylate (210 mg, 86%) as pale yellow solid. ¹H NMR (400 MHz, CD₃OD) δ 6.28 (s, 2H), 4.21-4.11 (m, 2H), 3.90 (d, J=7.0 Hz, 1H), 3.71 (d, J=7.0 Hz, 1H), 3.47-3.36 (m, 1H), 3.20-3.09 (m, 1H), 2.92-2.82 (m, 1H), 2.81-2.71 (m, 1H), 2.48-2.38 (m, 1H), 2.36-2.26 (m, 1H), 2.20-1.88 (m, 3H), 1.24 (d, J=6.0 Hz, 3H), 1.00 (t, J=7.0 Hz, 6H); LCMS (ESI): m/z 284.2 [M⁺+1-maleic acid]; HPLC: 97.98%; Melting point: 114.8° C.-118.3° C.

Example 3—Synthesis of Compound C

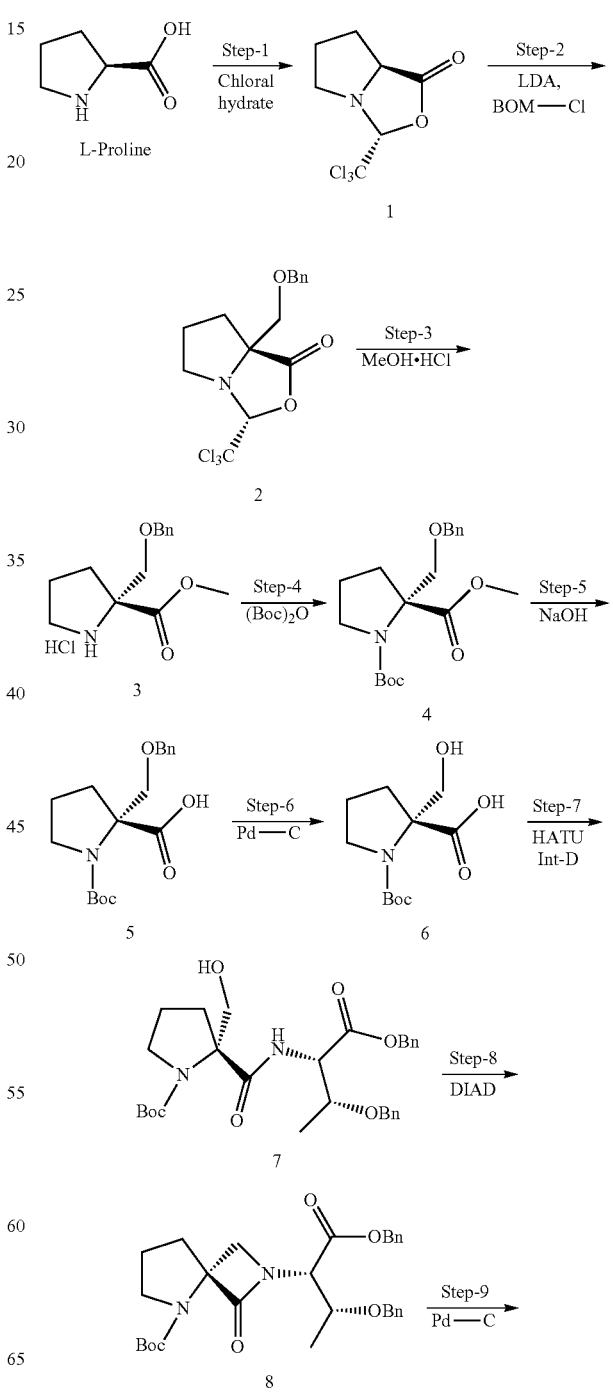

-continued

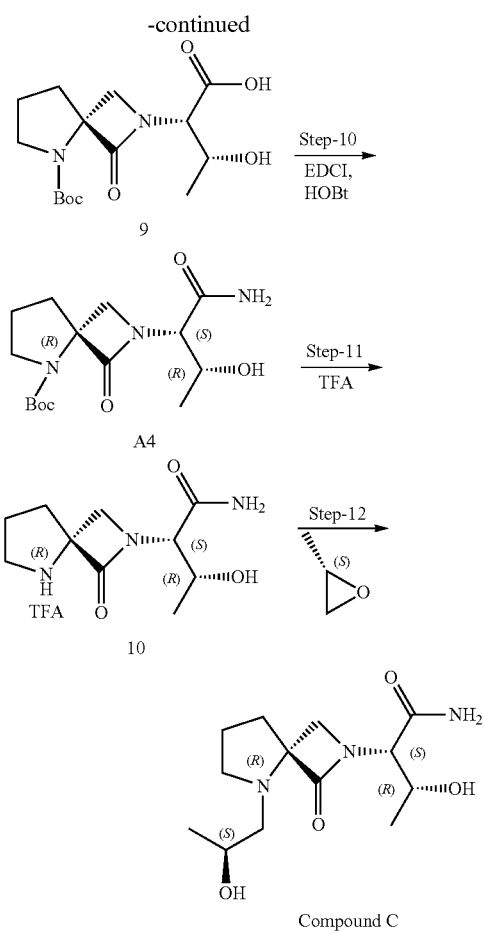

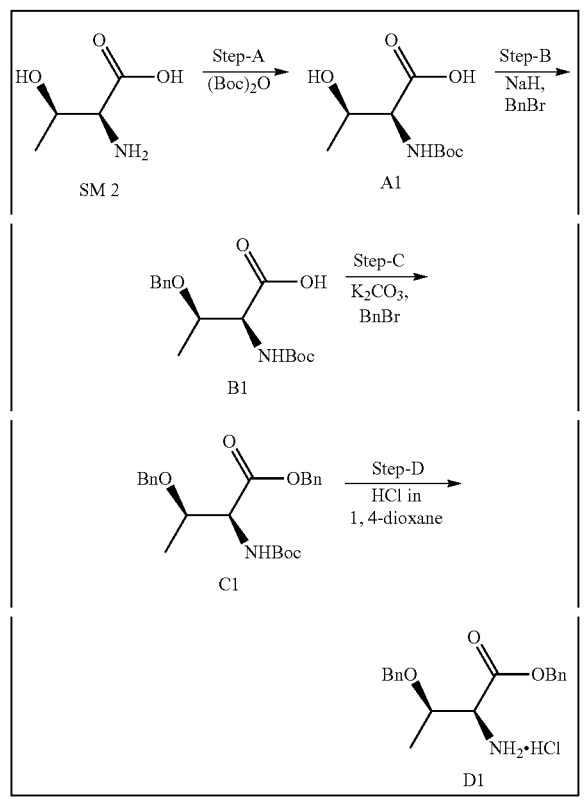

Synthesis of (3R,7aS)-3-(trichloromethyl)tetrahydro-1H,3H-pyrrolo[1,2-c]oxazol-1-one (1)

To a suspension of L-proline (2.0 kg, 0.017 mol) in chloroform (50 L) was added chloral hydrate (5.7 kg, 0.034 mol) at RT. The reaction mixture was heated to 60° C. under reverse Dean-Stark apparatus and obtained water was collected. After 16 h, the volatiles were concentrated under reduced pressure. Crude solid was washed with cold ethanol, filtered and dried to afford compound 1 (2.2 kg, 57%) as white solid. $^1$H-NMR: (500 MHz, DMSO-$d_6$): δ 5.82 (s, 1H), 4.11-4.08 (m, 1H), 3.33-3.27 (m, 2H), 3.19-3.14 (m, 1H), 2.15-2.10 (m, 1H), 1.96-1.91 (m, 1H), 1.80-1.74 (m, 1H), 1.65-1.58 (m, 1H).

Synthesis of (3R,7aR)-7a-((benzyloxy)methyl)-3-(trichloromethyl)tetrahydro-1H,3H-pyrrolo[1,2-c]oxazol-1-one (2)

To a solution of diisopropylamine (221.2 mL, 1.533 mol) in THF (870 mL) was added n-BuLi (1.6 M in hexane) (958.5 mL, 1.533 mol) drop wise at −78° C. under nitrogen atmosphere. After completion of addition, temperature of reaction mixture was raised to −20° C. and stirred for 1 h. Again cooled to −78° C., compound 1 (250 g, 1.022 mol) in THF (1 L) was added and stirred for 30 min. Then benzyl-chloromethyl ether (208 mL, 1.329 mol) was added drop wise and stirring continued for 1 h. After consumption of the starting material (by TLC), the reaction mixture was quenched with ice-cold water (100 mL) and extracted with $Et_2O$ (2×100 mL). Combined organic layers were washed with brine (100 mL), dried over anhydrous $Na_2SO_4$ and concentrated under reduced pressure which was purified by column chromatography by eluting with 10% EtOAC/n-hexane to obtain compound 2 (220 g, crude) as brown thick syrup. $^1$H-NMR: (500 MHz, DMSO-$d_6$): δ 7.42-7.26 (m, 5H), 5.60 (s, 1H), 4.59-4.53 (d, 2H), 3.67-3.61 (m, 2H), 3.37-3.33 (m, 1H), 3.31-3.10 (m, 1H), 2.12-1.99 (m, 2H), 1.87-1.75 (m, 2H); LCMS (ESI): m/z 363.9[M$^+$+1].

Synthesis of methyl (R)-2-((benzyloxy)methyl)pyrrolidine-2-carboxylate hydrochloride (3)

To a solution of compound 2 (400 g, 1.096 mol) in methanol (1 L) was added 2N HCl in MeOH (1.64 L, 3.29 mol) at RT and stirred at 80° C. for 16 h. After consumption of the starting material (by TLC), volatiles were evaporated under reduced pressure. Obtained crude was washed with hexanes (3×750 mL) and dried under reduced pressure to afford compound 3 (358 g, crude) as reddish thick syrup. $^1$H-NMR: (500 MHz, DMSO-$d_6$): δ 10.40 (br s, 1H), 7.40-7.21 (m, 5H), 4.64-4.50 (d, 2H), 4.49-4.3 (d, 2H), 3.76 (s, 3H), 3.33-3.22 (m, 2H), 2.22-2.15 (s, 1H), 2.02-1.9 (m, 2H), 1.95-1.83 (m, 1H).

Synthesis of 1-(tert-butyl) 2-methyl (R)-2-((benzyloxy)methyl)pyrrolidine-1,2-dicarboxylate (4)

To a stirred suspension of compound 3 (313 g, crude 1.096 mol) in DCM (2.19 L) was added $Et_3N$ (458.4 mL, 3.288 mol) drop wise at 0° C. under nitrogen atmosphere and stirred for 10 min. Then Boc-anhydride (358.4 g, 1.644 mol) was added drop wise at 0° C. The reaction mixture was brought to RT and stirred for 16 h. After consumption of the starting material (by TLC), the reaction was diluted with water (2×1 L) and extracted with $CH_2Cl_2$ (2×500 mL). The combined organic layer was washed with 10% citric acid (pH~7) and brine solution (1 L). The organic layer was dried over Na$_2$SO$_4$ and concentrated under reduced pressure to afford crude compound which was purified by column chromatography by eluting with 20% EtOAC/n-hexane to obtain compound 4 (215 g, 56%) as colorless thick syrup. $^1$H-NMR: (500 MHz, DMSO-d$_6$): δ 7.37-7.26 (m, 5H), 4.56-4.48 (m, 2H), 4.03-3.87 (dd, 1H), 3.69-3.67 (d, 1H), 3.62 (s, 3H), 3.53-3.47 (m, 1H), 3.33-3.30 (m, 1H), 2.27-2.20 (m, 1H), 2.03-1.89 (m, 2H), 1.88-1.79 (m, 1H), 1.46-1.24 (2s, 9H); LCMS (ESI): m/z 250.1 [(M$^+$+1)-Boc].

Synthesis of (R)-2-((benzyloxy)methyl)-1-(tert-butoxycarbonyl)pyrrolidine-2-carboxylic acid (5)

To a solution of compound 4 (215 g, 0.616 mol) in MeOH:THF:H$_2$O (3 L, 5:5:3) was added NaOH (73.9 g, 1.848 mol) and stirred at RT for 10 min. The reaction mixture was heated to 80° C. and stirred for 16 h. After consumption of the starting material (by TLC), reaction mixture was brought to RT, volatiles were evaporated. Crude material was diluted with water (1 L) and extracted with Et$_2$O (2×500 mL). The separated aqueous layer was acidified using 2 N HCl solution (pH-3) and extracted with DCM (2×750 mL).

Combined organic layers were washed with brine solution, dried over Na$_2$SO$_4$ and concentrated to afford compound 5 (170 g, 82.4%) as off white solid. $^1$H-NMR: (500 MHz, DMSO-d$_6$): δ 12.66 (br s, 1H), 7.36-7.26 (m, 5H), 4.54-4.47 (m, 2H), 4.05-3.90 (dd, 1H), 3.88-3.63 (d, 1H), 3.63-3.44 (m, 1H), 3.34-3.27 (m, 1H), 2.27-2.01 (m, 1H), 2.02-1.8 (m, 2H), 1.79-1.76 (m, 1H), 1.17-1.14 (2s, 9H); LCMS (ESI): m/z 235.1[(M$^+$+1)-Boc].

Synthesis of (R)-1-(tert-butoxycarbonyl)-2-(hydroxymethyl)pyrrolidine-2-carboxylic acid (6)

To a stirring solution of compound 5 (170 g, 0.507 mol) in CH$_3$OH (1 L) was added 50% wet 10% Pd—C(68 g) at RT and stirred for 16 h under H$_2$ atmosphere. After consumption of the starting material (by TLC), the reaction mixture was filtered through a pad of celite and the pad was washed with CH$_3$OH (1 L). Obtained filtrate was concentrated under reduced pressure to afford compound 6 (110 g, 88%) as white solid. $^1$H-NMR: (400 MHz, DMSO-d$_6$): δ 12.66 (br s, 1H), 3.96-3.83 (dd, 1H), 3.63-3.60 (m, 1H), 3.49-3.46 (m, 1H), 3.34-3.25 (m, 2H), 2.30-2.15 (m, 1H), 1.95-1.72 (m, 3H), 1.38-1.33 (2s, 9H); LCMS (ESI): m/z 244 [M$^+$-1]; Chiral HPLC: 95.88%.

Synthesis of tert-butyl (R)-2-(((2S,3R)-1,3-bis(benzyloxy)-1-oxobutan-2-yl)carbamoyl)-2-(hydroxymethyl)pyrrolidine-1-carboxylate (7)

To a stirring solution of compound 6 (110 g, 0.448 mol) in DCM (20 mL) reaction mixture cooled to 0° C. under N$_2$ atmosphere diisopropylethylamine (206 mL, 1.12 mol) were added intermediate D1 (150 g, 0.448 mol), HATU (204 g, 0.537 mol) under nitrogen atmosphere. The reaction mixture was brought to RT and stirred for 4 h. After consumption of the starting material (by TLC), the reaction mixture was diluted with DCM (1 L) and washed with water (2×500 mL), 10% citric acid solution (500 mL) and brine solution (500 mL). Organic layer was dried over anhydrous Na$_2$SO$_4$ and concentrated under reduced pressure to afford crude compound which was purified by column chromatography by eluting with 30% EtOAc/n-hexane to obtain compound 7 (143 g, 60%) as colorless thick syrup. $^1$H-NMR: (500 MHz, DMSO-d$_6$): δ 8.20-8.12 (d, 1H), 7.29-7.18 (m, 10H), 5.83-5.59 (m, 1H), 5.08 (s, 2H), 4.50-4.44 (m, 2H), 4.30-4.26 (m, 1H), 4.08-4.00 (m, 2H), 3.42-3.40 (m, 2H), 3.39-3.29 (m, 1H), 2.19-2.08 (m, 1H), 1.96-1.87 (m, 1H), 1.68-1.63 (m, 2H), 1.23-1.15 (2s, 9H), 1.14-1.13 (d, 3H); LCMS (m/z): 525.2 [M$^+$−1]; HPLC: 76.2%; Chiral HPLC: 69.47%.

Synthesis of tert-butyl (R)-2-((2S,3R)-1,3-bis(benzyloxy)-1-oxobutan-2-yl)-1-oxo-2,5-diazaspiro[3.4]octane-5-carboxylate (8)

To a solution of triphenylphosphine (161.4 g, 0.612 mol) in THF (430 mL) was added DIAD (123.8 g, 0.612 mol) drop wise at RT under nitrogen atmosphere and stirred for 15 minutes. To this, compound 7 (215 g, 0.408 mol) in THF (860 mL) solution was added drop wise and allowed to stir RT for 4 h. After consumption of the starting material (by TLC), volatiles were evaporated under reduced pressure. Obtained crude material was purified by silica gel column chromatography eluting with 20% EtOAc/hexane to afford compound 8 (180 g, mixture with DIAD by product) as yellow syrup. $^1$H-NMR: (400 MHz, DMSO-d$_6$): δ 7.31-7.18 (m, 10H), 5.18-5.10 (m, 2H), 4.61-4.54 (m, 2H), 4.27-4.18 (m, 2H), 3.78-3.77 (d, 1H), 3.45-3.43 (d, 1H), 3.35-3.31 (d, 1H), 3.27-3.23 (m, 1H), 2.03-1.98 (m, 2H), 1.78-1.76 (m, 2H), 1.39-1.31 (2s, 9H), 1.23-1.22 (d, 3H) (DIAD by product peaks were not captured); LCMS (ESI): m/z 509.4 [M$^+$+1].

Synthesis of (2S,3R)-2-((R)-5-(tert-butoxycarbonyl)-1-oxo-2,5-diazaspiro[3.4]octan-2-yl)-3-hydroxybutanoic acid (9)

A solution of compound 8 (85 g, 0.167 mol) in methanol (850 mL) was degassed under N$_2$ atmosphere. Then added 50% wet 10% Pd—C(40 g) at RT and stirred for 24 h under H$_2$ atmosphere. After consumption of the starting material (by TLC), the reaction mixture was filtered through a pad of celite and filtrate was concentrated under reduced pressure. Obtained crude solid was diluted with Et$_2$O (1 L) and vigorously stirred at RT for 1 h. Resultant solid material was filtered off and dried to afford compound 9 (75 g, 68%) as white solid. $^1$H-NMR: (400 MHz, DMSO-d$_6$): δ 12.86 (br s, 1H), 5.24 (br s 1H), 4.06-4.00 (m, 2H), 3.88-3.82 (m, 1H), 3.51-3.50 (m, 1H), 3.43-3.34 (m, 1H), 3.31-3.23 (m, 1H), 2.15-2.09 (m, 2H), 1.82-1.78 (m, 2H), 1.39-1.31 (2s, 9H), 1.10-1.08 (d, 3H); LCMS (m/z): 329.1 [M$^+$+1]; HPLC: 93.97%.

Synthesis of tert-butyl (R)-2-((2S,3R)-1-amino-3-hydroxy-1-oxobutan-2-yl)-1-oxo-2,5-diazaspiro[3.4]octane-5-carboxylate (A4)

To a stirring solution of compound 9 (150 g, 0.457 mol) in CH$_2$Cl$_2$ (2 L) cooled the reaction mixture to 0° C. were added diisopropylethylamine (176.85 g, 1.37 mol), NH$_4$Cl (48.8 g, 0.914 mol) and HATU (208.3 g 0.548 mols) under nitrogen atmosphere. The reaction mixture was brought to RT and stirred for 12 h. After consumption of the starting material (by TLC), the reaction mixture was diluted with water (2×750 mL) and extracted with CH$_2$Cl$_2$ (2×1 L). Combined organic layer was washed with 2N HCl solution and saturated sodium chloride solution (750 mL). Organic layer was dried over anhydrous Na$_2$SO$_4$ and concentrated under reduced pressure. Crude compound was purified by column chromatography pure compound was eluting with 3% MeOH/CH$_2$Cl$_2$. The obtained material was diluted with DCM (2 L) and washed with saturated citric acid (5×500 mL), saturated bicarbonate wash followed by brine wash and dried over $Na_2SO_4$. The material was triturated with the ether (2×500 mL) to afford compound A4 (80 g, 53%) as white solid. $^1$H-NMR: (400 MHz, $D_2O$): δ 4.36-4.21 (m, 2H), 4.03-3.98 (m, 1H), 3.76-3.67 (m, 1H), 3.56-3.37 (m, 2H), 2.32-2.23 (m, 2H), 1.97-1.93 (m, 2H), 1.49-1.47 (2s, 9H), 1.33-1.32 (d, 3H); LCMS (ESI): m/z 328.3 [$M^+$+1]; HPLC: 99.30%; Chiral HPLC: 98.97%; SOR (c=1, $CH_3OH$): −11.08.

Synthesis of (2S,3R)-3-hydroxy-2-((R)-1-oxo-2,5-diazaspiro[3.4]octan-2-yl)butanamide (10)

To a stirring solution of compound A4 (2 g, 6.16 mmol) in $CH_2Cl_2$ (10 mL) was added TFA (1.0 mL, 12.2 mmol) at 0° C. under nitrogen atmosphere. The reaction mixture was brought to RT and stirred for 2 h. After consumption of the starting material (by TLC), volatiles were evaporated under reduced pressure. Obtained thick syrup material was washed with ether (2×50 mL) and dried under vacuum to afford crude compound 10 (2.5 g, TFA salt) as thick syrup, which was taken to next step. $^1$H NMR (500 MHz, $CD_3OD$): δ 4.24-4.17 (m, 2H), 3.99-3.89 (m, 2H), 3.52-3.39 (m, 2H), 2.46-2.32 (m, 2H), 2.26-2.10 (m, 2H), 1.28 (d, J=6.1 Hz, 3H); LCMS (ESI): m/z 228.1 [$M^+$+1].

Synthesis of (2S,3R)-3-hydroxy-2-((R)-5-((S)-2-hydroxypropyl)-1-oxo-2,5-diazaspiro[3.4]octan-2-yl)butanamide (Compound C)

To a stirring solution of compound 10 (TFA salt, 2 g, 5.86 mmol) in methanol (10 mL) was added NaOMe (630 mg, 11.7 mmol) followed by (S)-2-methyloxirane (510 mg, 8.79 mmol) at RT under nitrogen atmosphere. The reaction mixture was stirred at RT for 24 h. After consumption of the starting material (by TLC), the reaction mixture was diluted with $CH_2Cl_2$ (10 mL) and concentrated under reduced pressure. Obtained crude material was purified by silica gel column chromatography eluting with 5% MeOH/DCM to afford (2S,3R)-3-hydroxy-2-((R)-5-((S)-2-hydroxypropyl)-1-oxo-2,5-diazaspiro[3.4]octan-2-yl)butanamide (185 mg, 12%) as thick syrup. $^1$H NMR (400 MHz, $CD_3OD$): δ 4.18-4.07 (m, 2H), 3.90-3.81 (m, 1H), 3.63 (d, J=6.1 Hz, 1H), 3.58 (d, J=6.1 Hz, 1H), 3.11 (dt, J=4.2, 8.2 Hz, 1H), 2.83-2.67 (m, 2H), 2.62-2.54 (m, 1H), 2.26-2.12 (m, 2H), 1.98-1.83 (m, 2H), 1.24 (d, J=6.1 Hz, 3H), 1.14 (d, J=6.3 Hz, 3H); LCMS (ESI): m/z 285.9 [$M^+$+1]; HPLC: 97.20%.

Example 4

This example demonstrates the positive emotional learning (PEL) test. Experiments were conducted as described in Burgdorf et al., "The effect of selective breeding for differential rates of 50-kHz ultrasonic vocalizations on emotional behavior in rats," Devel. Psychobiol., 51:34-46 (2009). Rat 50-kHz ultrasonic vocalization (hedonic USVs) is a validated model for the study of positive affective state and is best elicited by rough-and-tumble play. 50-kHz ultrasonic vocalizations have previously been shown to be positively correlated with reward and appetitive social behavior in rats, and to reflect a positive affective state.

The PEL assay measures the acquisition of positive (hedonic) 50-kHz ultrasonic vocalizations (USVs) to a social stimulus, heterospecific rough and tumble play stimulation. Heterospecific rough-and-tumble play stimulation was administered by the experimenter's right hand. Animals received 3 min of heterospecific rough-and-tumble play that consisted of alternating 15 sec blocks of heterospecific play and 15 sec of no-stimulation. High frequency ultrasonic vocalizations (USVs) were recorded and analyzed by sonogram with Avasoft SASlab Pro (Germany) as previously described by Burgdorf et al., "Positive emotional learning is regulated in the medial prefrontal cortex by GluN2B-containing NMDA receptors," Neuroscience, 192:515-523 (2011). Frequency modulated 50-kHz USVs that occurred during each of the no-stimulation periods were quantified to measure PEL. Animals were not habituated to play stimulation before testing. Positive emotional learning was measured during the conditioned stimulus (CS) trials preceding the tickle unconditioned stimulus (UCS) trials. Animals received 15 second trials consisting of 6 CS and 6 UCS trials each (3 min total). Running speed for animals to self administer tickling at the end of the 3 min session was also measured.

FIG. 1 shows the results of the rat PEL test. The results demonstrate that Compound A, when administered one hour prior to PEL testing, increases positive emotional learning as measured by rat USVs, thereby indicating an antidepressant effect.

Example 5

Microsomal and plasma stability of Compound A was investigated. The following table indicates the percent of Compound A remaining after 60 minutes.

|  | Human | Rat |
| --- | --- | --- |
| Microsomal | 86% | 65% |
| Plasma | 100% | 92% |

Unbound drug concentration in the brain was also investigated, and plasma protein binding assays were conducted. The following table (% bound) indicates results for Compound A.

| Human | Rat |
| --- | --- |
| 25.9% | 29.95% |

The bioavailablity of Compound A was investigated following PO administration. CSF, brain and plasma samples were analyzed following dosing with compound A (10 mg/kg). The following table indicates the bioavailablity and CSF/plasma and brain/plasma ratios.

| | |
| --- | --- |
| Bioavailablity (% F) | 42 |
| CSF/plasma ratio | 0.65 |
| Brain/plasma ratio | 0.19 |

Example 6

Assays were conducted as described by Moskal et al., "GLYX-13: a monoclonal antibody-derived peptide that acts as an N-methyl-D-aspartate receptor modulator," Neuropharmacology, 49, 1077-87, 2005. The potentiation of [$^3$H] MK-801 binding (5 nM; 22.5 Ci/mmol) to well washed rat cortical membranes (200 μg) was measured under non-equilibrium conditions (15 min @ 25° C.) in the presence of increasing concentrations of Compound A.

Figure 2:
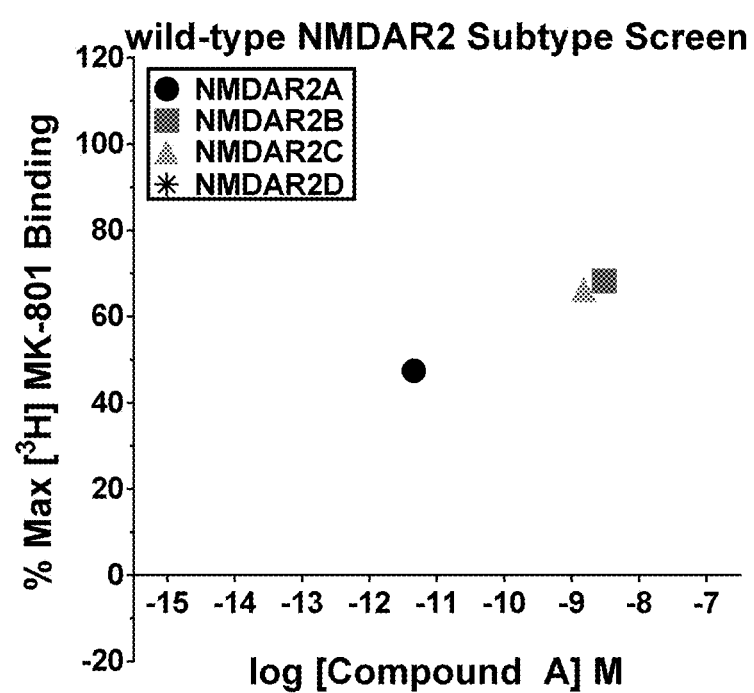
FIG. 2 depicts the potentiation of [3H]MK-801 binding for wild-type NMDAR2 subtypes for compound A.

FIG. 2 depicts the the potentiation of [$^3$H]MK-801 binding for wild-type NMDAR2 subtypes for A. As shown in FIG. 2, Compound A is highly NR2A preferring with no binding to NR2D.

Example 7

Sprague Dawley rats were dosed intravenously with 2 mg/kg of Compound A. A second group of Sprague Dawley rats was dosed per os with 10 mg/kg of compound A. Plasma samples were drawn over a 24 h period and analyzed for Compound A.

Figure 3:
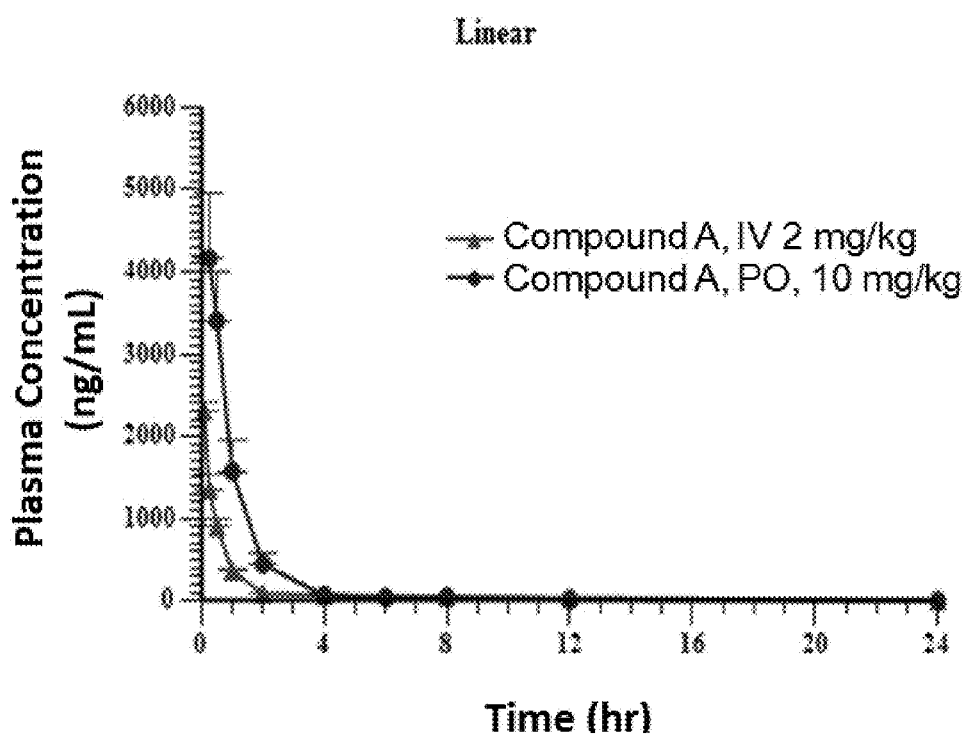
FIG. 3 depicts the mean plasma concentration-time profile of compound A following a single intraveneous (2 mg/kg) and oral (10 mg/kg) dose administration in male Sprague Dawley rats.

FIG. 3 presents the mean plasma concentration-time profile of Compound A following the single intraveneous (2 mg/kg) and oral (10 mg/kg) dose administration in male Sprague Dawley rats over the 24 hour period.

In another experiment, Sprague Dawley rats were dosed per os with 10 mg/kg of Compound A. Plasma, brain, and CSF samples were analyzed at various time points over a 24 hour period.

Figure 4:
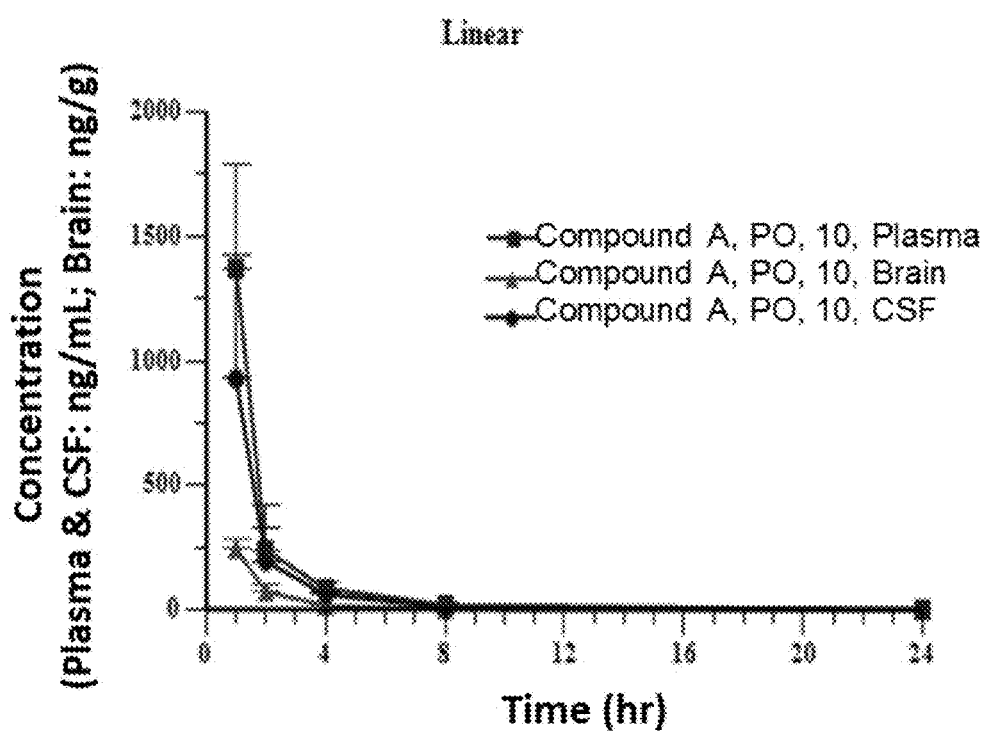
FIG. 4 depicts the mean plasma, brain, and CSF concentration-time profile of compound A following a single oral (10 mg/kg) dose administration in male Sprague Dawley rats.

FIG. 4 displays the mean plasma, brain, and CSF concentration-time profile of Compound A following a single oral (10 mg/kg) dose administration in male Sprague Dawley rats over the 24 hour period.

Example 8

This example relates to the PEL experiment, as stated above in Example 3. Rat ultrasonic vocalizations (USVs) test.

Positive emotional learning was measured during the conditioned stimulus (CS) trials preceding the tickle unconditioned stimulus (UCS) trials. Animals received 15 second trials consisting of 6 CS and 6 UCS trials each (3 min total).

Figure 5:
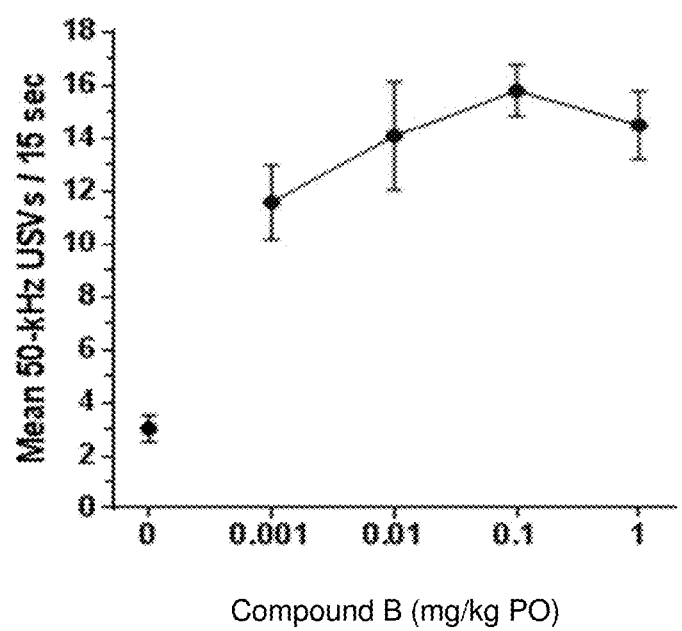
FIG. 5 depicts the mean 50-kHz USV data for compound B in a PEL model

FIG. 5 shows the results of the rat USVs test. The results demonstrate that Compound B increases positive emotional learning in the rat USVs test, thereby indicating an antidepressant effect.

Example 9

Microsomal and plasma stability of Compound B was investigated. The following table indicates the percent of Compound B remaining after 60 minutes.

|            | Human | Rat |
|------------|-------|-----|
| Microsomal | 87%   | 81% |
| Plasma     | 100%  | 89% |

Unbound drug concentration in the brain was also investigated, and plasma protein binding assays were conducted. The following table (% bound) indicates results for Compound B.

| Human | Rat   |
|-------|-------|
| 28.8% | 19.8% |

The bioavailablity of Compound B was investigated. CSF, brain and plasma samples were analyzed following dosing with Compound B. The following table indicates the bioavailablity and CSF/plasma and brain/plasma ratios.

| Bioavailablity (% F) | 38   |
|----------------------|------|
| CSF/plasma ratio     | 0.70 |
| Brain/plasma ratio   | 0.18 |

Compound A and Compound B both have lower oral bioavailability but a higher proportion is able to get to the CSF and brain.

Example 10

Figure 6:
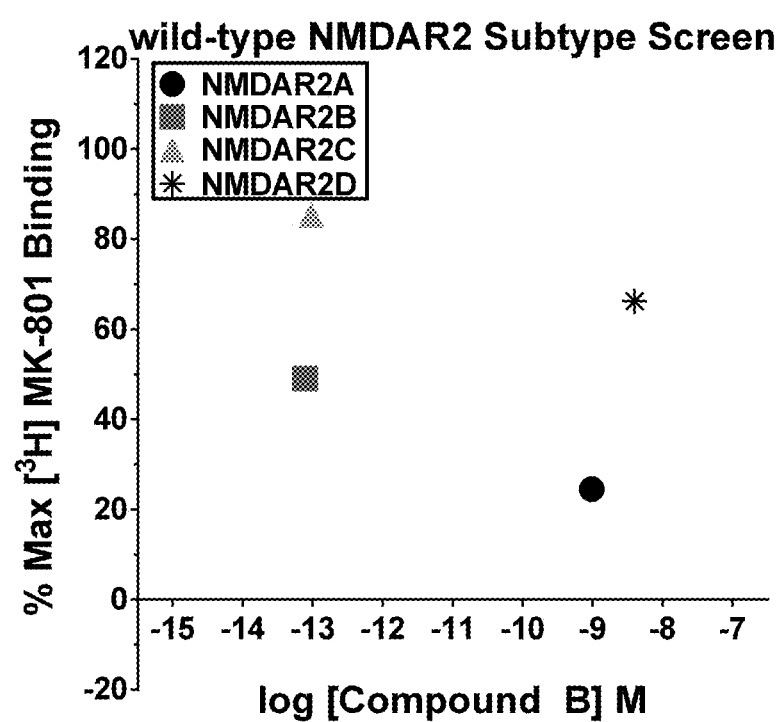
FIG. 6 depicts the potentiation of [3H]MK-801 binding for wild-type NMDAR2 subtypes for compound B.

Assays were conducted as described above in Example 5, by Moskal et al. (2005). The potentiation of [$^3$H]MK-801 binding (5 nM; 22.5 Ci/mmol) to well washed rat cortical membranes (200 μg) was measured under non-equilibrium conditions (15 min @ 25° C.) in the presence of increasing concentrations of compound B. FIG. 6 depicts the the potentiation of [$^3$H]MK-801 binding for wild-type NMDAR2 subtypes for compound B. Compound B is highly NR2B and NR2D preferring with lower potency in NR2A and NR2C.

Example 11

Sprague Dawley rats were dosed intravenously with 2 mg/kg of Compound B. A second group of Sprague Dawley rats was dosed per os with 10 mg/kg of Compound B. Plasma samples were drawn over a 24 h period and analyzed for compound B.

Figure 7:
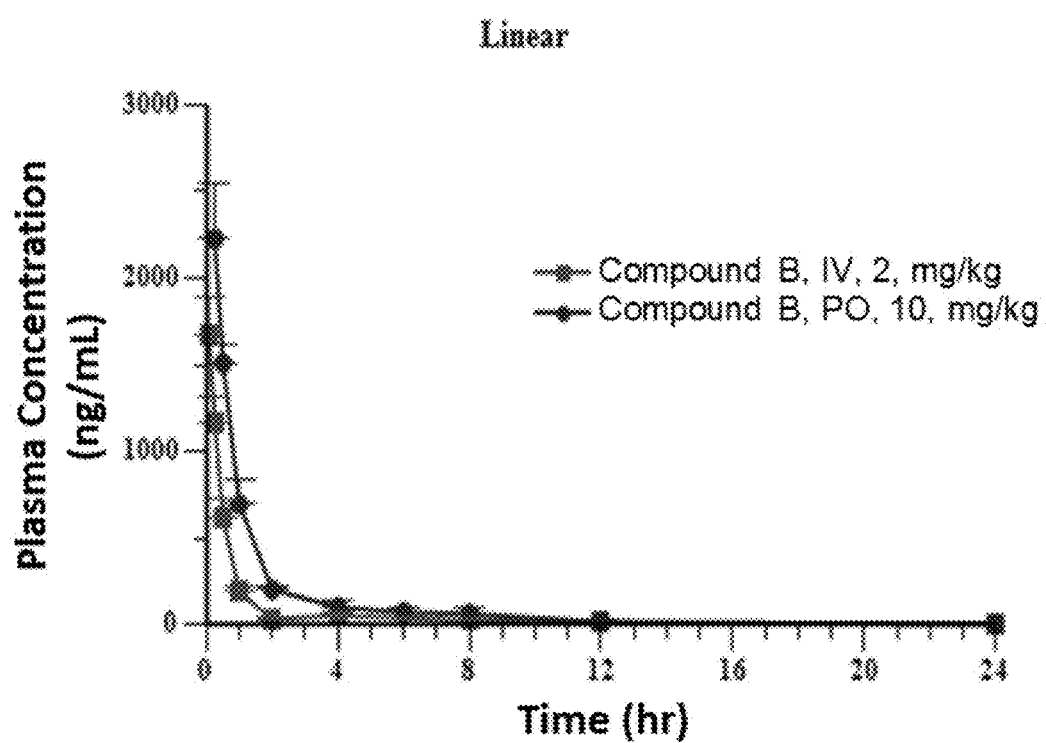
FIG. 7 depicts the mean plasma concentration-time profile of compound B following a single intraveneous (2 mg/kg) and oral (10 mg/kg) does administration in male Sprague Dawley rats.

FIG. 7 depicts the mean plasma concentration-time profile of Compound B following a single intraveneous (2 mg/kg) and oral (10 mg/kg) dose administration in male Sprague Dawley rats over a 24 hour period.

In another experiment, Sprague Dawley rats were dosed per os with 10 mg/kg of compound B. Plasma, brain, and CSF samples were analyzed at various time points over the 24 hour period.

Figure 8:
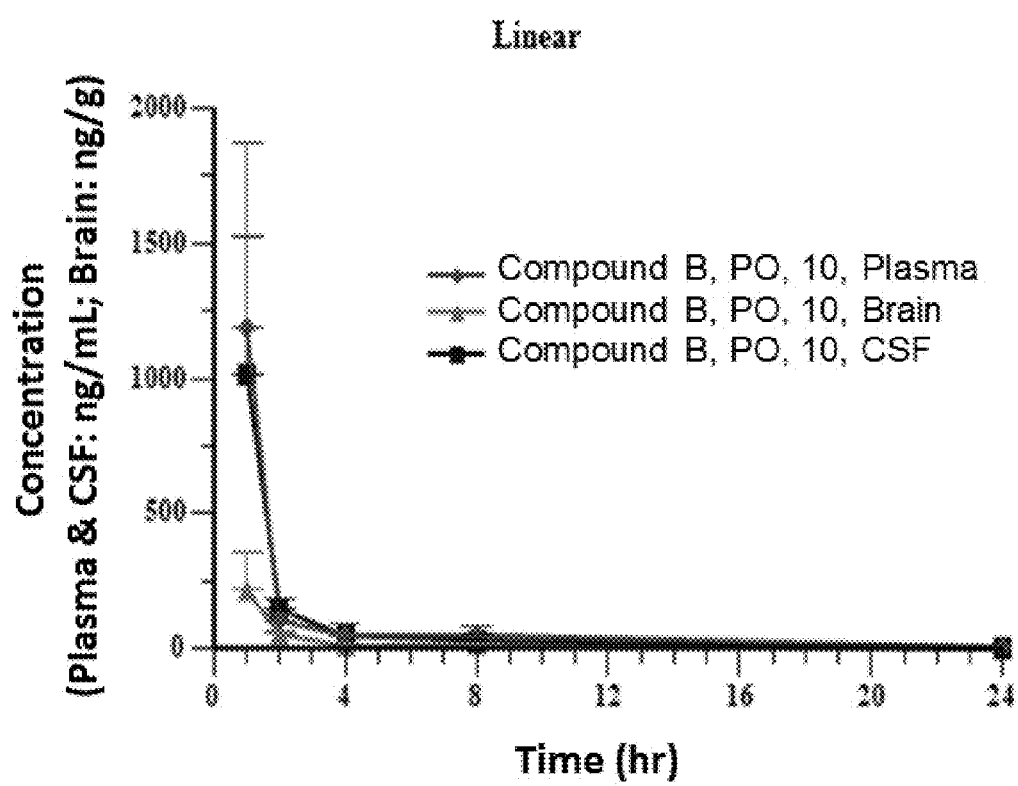
FIG. 8 depicts the mean plasma, brain, and CSF concentration-time profiles of compound B following a single oral (10 mg/kg) dose administration in male Sprague Dawley rats.

FIG. 8 depicts the mean plasma, brain, and CSF concentration-time profiles of Compound B following a single oral (10 mg/kg) dose administration in male Sprague Dawley rats over the 24 hour period.

Example 12

The in vitro MN (micronucleus) assay was performed for Compound A. The assay was also performed for Compound B. Cytotoxicity is presented as the % of control growth. A cytotoxicity value of less than 60% is flagged, and the compound is considered toxic at the respective concentration. The results of the in vitro MN assay for Compound A are shown in FIG. 9. The results of the in vitro MN assay for Compound B are shown in FIG. 10.

The Ames assay was performed for each of Compound A and Compound B. For the Ames assay results, hyphens (−) indicate negative results. Weak positives, if p<0.05, are denoted as "+". Strong positives, if p<0.01, are denoted as "++". Very strong positives, if p<0.001, are denoted as "+++". The results of the Ames assay for Compound A are shown in FIG. 9. The results of the Ames assay for Compound B are shown in FIG. 10.

A hERG assay was performed using Compound A to identify potential hERG channel interactions. Also, a hERG assay was performed using Compound B. For hERG, results showing an inhibition or stimulation higher than 50% are considered to represent significant effects on the test compound. The results of the hERG assay for Compound A are shown in FIG. 9 and the results of the hERG assay for Compound B are shown in FIG. 10.

Example 13

Single blast-induced traumatic brain injury/cognitive deficits were induced, modified for use in rats according to the protocol of Goldstein et al., "Chronic traumatic encephalopathy in blast-exposed military veterans and a blast neurotrauma mouse model," Science Translational Medicine, Vol. 4, Issue 134, pp. 134ra60, 2012. Male 2-3 month old Sprague Dawley rats were used. Rats were housed in Lucite cages with aspen wood chip bedding, maintained on a 12:12 light:dark cycle (lights on at 5 AM), and given ad libitum access to Purina lab chow (USA) and tap water throughout the study. Rats were first anesthetized using 3.5-4% isoflurane, then the ears were protected with 1.5×1.5 mm foam plugs (Pura-Fit®, Moldex-Metric Inc., Culver City, Calif.), and the rat was placed into a head access rodent thoracic restrainer (Stoelting, USA) to protect the body while allowing the head to move freely. An aluminum shock tube (183×61 cm; L-3 Applied Technologies, USA) was positioned 10 cm from the head of the rat. Rats received a single ~42 PSI blast of helium generated by puncturing 0.014 inches of polyester film. Sham controls were placed outside of the blast radius. Animals were dosed with Compound A (10 mg/kg PO), Compound B (10 mg/kg PO) or 0.5% Na-CMC in 0.9% sterile saline vehicle (1 ml/kg PO) 1 h post-blast.

PEL (Positive emotional learning) was conducted 48 hours post-blast. Heterospecific rough-and-tumble play was conducted as previously described by Burgdorf et al., "The long-lasting antidepressant effects of rapastinel (GLYX-13) are associated with a metaplasticity process in the medial prefrontal cortex and hippocampus," Neuroscience 308:202-211, 2015. Heterospecific rough-and-tumble play stimulation was administered by the experimenter's right hand. Animals received 3 min of heterospecific rough-and-tumble play that consisted of alternating 15 sec blocks of heterospecific play and 15 sec of no-stimulation. High frequency ultrasonic vocalizations (USVs) were recorded and analyzed by sonogram with Avasoft SASlab Pro (Germany) as previously described by Burgdorf et al., "Positive emotional learning is regulated in the medial prefrontal cortex by GluN2B-containing NMDA receptors," Neuroscience, 192: 515-523, 2011. Frequency modulated 50-kHz USVs that occurred during each the no-stimulation periods were quantified to measure PEL. Animals were not habituated to play stimulation before testing.

Figure 11:
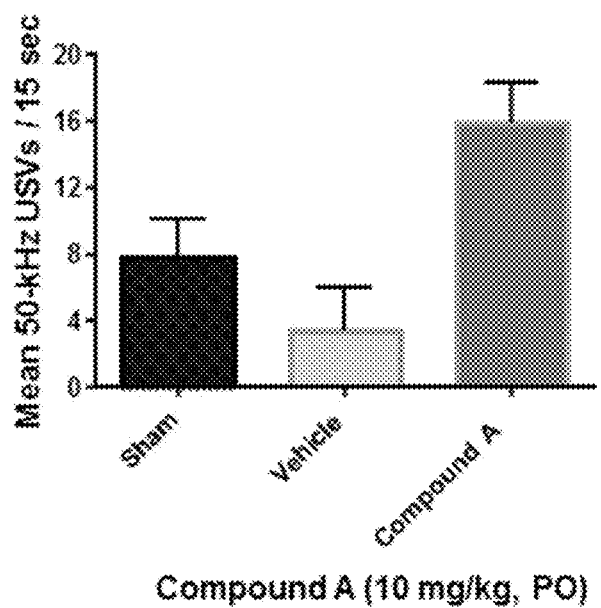
FIG. 11 depicts the reversed blast-induced cognitive deficits as measured by PEL for Compound A.
Figure 12:
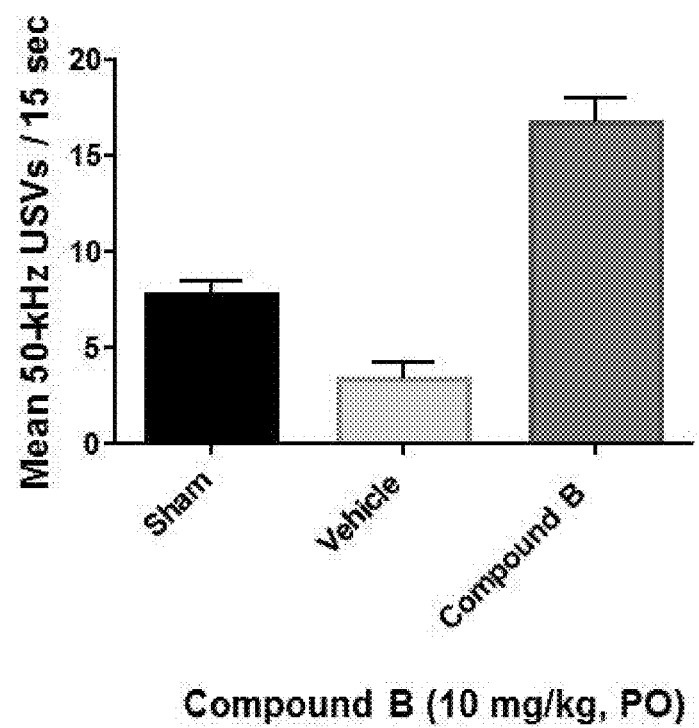
FIG. 12 depicts the reversed blast-induced cognitive deficits as measured by PEL for Compound B.

The results of the PEL study for Compounds A and B are reported in FIGS. 11 and 12.

Example 14

This Example relates to the assessment of the anxiolytic effect of treatment in the stress-induced anxiety model, novelty induced hypophagia. This assay is also sensitive to the rapid acting antidepressants ketamine and GLYX-13 (Li et al., "mTOR-dependent synapse formation underlies the rapid antidepressant effects of NMDA antagonists," Science 329:959-964, 2010; and Burgdorf et al., 2013). See also Bodnoff et al., "A comparison of the effects of diazepam versus several typical and atypical anti-depressant drugs in an animal model of anxiety," Psychopharmacology, 97:277-279, 1989.

Testing was conducted as described by (Burgdorf et al., 2013). A version of the novelty induced hypophagia (NIH) test was used that has previously been shown to detect the acute anxiolytic-like effect of ketamine (Li et al., 2010). Animals were food deprived overnight before testing, and lab chow was placed in the center chamber of an open field (40×40×20 cm) for 10 min under dim red lighting. Between testing each animal, feces and urine were removed from the apparatus. After NIH testing, the latency to eat in the animal's home cage was determined as a control to ensure the effect on eating is specific to the novel environment. Animals were videotaped, and latency (sec) for the animal to take the first bite of food was manually scored offline.

A single point per dose group that was 2 or more standard deviations from the mean was considered an outlier and was excluded from the data analysis. $ED_{50}$ was defined as the dose (or log linear interpolation of dose) that exhibited a half maximal effect (average of the vehicle and maximally efficacious dose) from a log (dose) linear (NIH value) plot. The maximally efficacious dose was defined as the lowest dose that was statistically different from vehicle but statistically equivalent (per Fisher's PLSD; a set at 0.05) to the higher doses.

Figure 13:
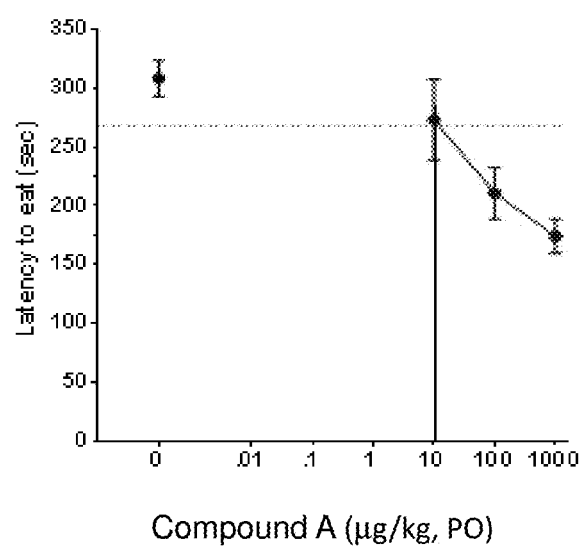
FIG. 13 depicts the results for the novelty-induced hypophagia (NIH) test in rats for Compound A.
Figure 14:
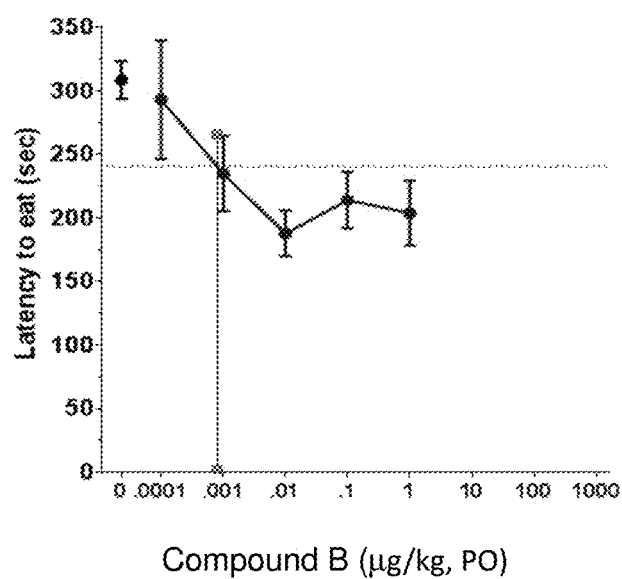
FIG. 14 depicts the results for the novelty-induced hypophagia (NIH) test in rats for Compound B.

The results are shown in FIGS. 13 and 14. As shown in FIG. 13, Compound A produces an anxiolytic effect in the novelty-induced hypophagia (NIH) test in rats. Mean±SEM latency to eat in the Novelty-Induced Hypophagia (NIH) test in 2-3 month old male SD rats treated with Compound A (10-1000 µg/kg PO; blue circles) or sterile saline+0.5% Na-CMC vehicle (1 ml/kg PO; black circle) 1 h before a single 10-min test session. Animals were food deprived overnight before testing, and lab chow was placed into the center chamber of the open field during testing.

As shown in FIG. 14, Compound B produces an anxiolytic effect in the novelty-induced hypophagia (NIH) test in rats. Mean±SEM latency to eat in the Novelty-Induced Hypophagia (NIH) test in 2-3 month old male SD rats treated with Compound B (0.0001-1 µg/kg PO; blue circles) or sterile saline+0.5% Na-CMC vehicle (1 ml/kg PO; black circle) 1 h before a single 10-min test session. Animals were food deprived overnight before testing, and lab chow was placed into the center chamber of the open field during testing.

Example 15

The Bennett model of mechanical analgesia is used to assess the analgesic effects of compounds as measured by paw withdrawal threshold. Bennett G J, Xie Y K, "A peripheral mononeuropathy in rat that produces disorders of pain sensation like those seen in man," Pain 33:87-107, 1988. Spared nerve injury surgery is performed on animals with testing for analgesic response once animals have recovered from surgery but still exhibit a low threshold of paw withdrawal after application of von frey filaments. Vehicle animals receive the surgery and then receive vehicle rather than test compound. Animals were tested 1 hr, 24 h and 1 wk post-test compound or vehicle administration.

Male 2-3 month old Sprague Dawley rats were used. Harlan was the supplier for all studies. Rats were housed in Lucite cages with aspen wood chip bedding, maintained on a 12:12 light:dark cycle (lights on at 5 AM), and given ad libitum access to Purina lab chow (USA) and tap water throughout the study.

Rats were anesthetized using inhaled isoflurane (2.5%). Spared nerve injury surgery was performed as previously described (Bennett and Xie, 1988). An incision (~1.5 cm in length) was made with a scalpel blade dorsally through skin on the right hindlimb, parallel and posterior to femur. Using a small pointed hemostat, the biceps femoris and gluteus superficialis muscles were separated. Using curved blunt forceps, the common sciatic nerve was isolated and exposed. For the mechanical analgesia studies, the whole sciatic nerve was ligated. Using hemostats/forceps and chromic gut (5-0), the nerve was loosely ligated with a square knot; 3 ligatures, 1 mm apart were placed on the nerve. The ligatures were tightened to the point that the suture did not slide up or down the nerve. This protocol resulted in a partial loss-of-function of the nerve. For the thermal analgesia studies, the common peroneal and tibial branches of the sciatic nerve were ligated and cut, and the sural branch was spared. See Decosterd I, Woolf C J, "Spared nerve injury: an animal model of persistent peripheral neuropathic pain," Pain 87:149-158, 2000. Testing occurred 1-2 weeks post-surgery.

During testing, rats were acclimated to the surface of a suspended wire mesh grid (1 cm×1 cm, with the wire being 0.3 cm in diameter) for 15-20 min. Starting from the smallest, each Von Frey filament was pressed perpendicularly to the plantar surface of the affected (ipsilateral) hindpaw until slightly bent and then held for 6 second. If an obvious hind paw withdrawal or a flinching behavior immediately after the withdrawal of the filament was not observed, the next larger filament was used in the same manner. In case of a response, a lower filament was used. This was repeated until six responses were collected.

Figure 15:
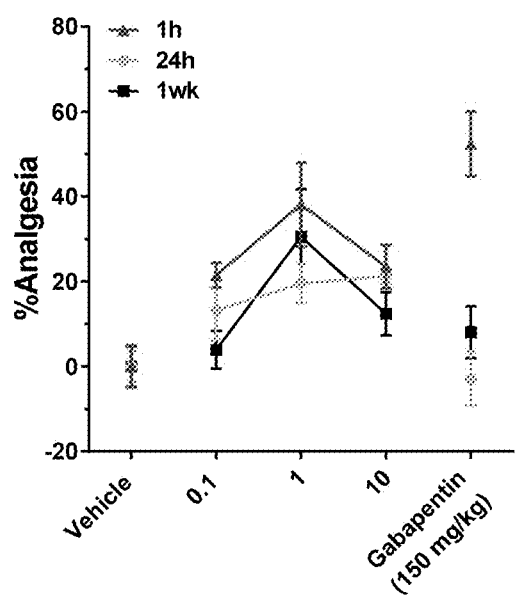
FIG. 15 depicts the analgesic effects of Compound A.
Figure 16:
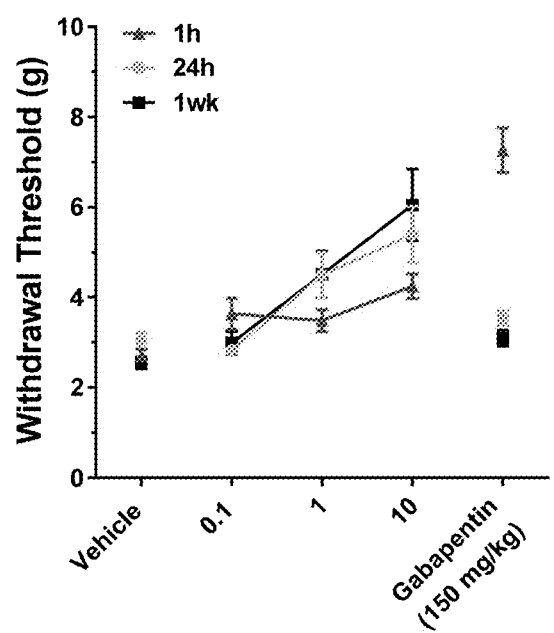
FIG. 16 depicts the analgesic effects of Compound B.

Testing occurred 1 h post-dosing with Compound A and Compound B (0.1-10 mg/kg PO), gabapentin (150 mg/kg PO) or 0.5% Na-CMC in 0.9% sterile saline. Animals were retested 24 hrs and 1 week post-dosing. The results for Compound A are shown in FIG. 15 and the results for Compound B are shown in FIG. 16. For both compounds, a single dose of 10 mg/kg PO produced a mechanical analgesic effect in the Bennett model 1 hr, 24 hrs and 1 week post-dosing whereas gabapentin only produced an analgesic effect 1 h post-dosing.

Example 16

A non-clinical in vivo pharmacology study (Porsolt assay) was performed to measure antidepressant-like effects. A negative control (0.5% sodium carboxymethyl cellulose in 0.9% sterile saline vehicle) and a positive control (Compound D) were used to compare against Compound A and Compound B. The study allowed for the construction of a dose-response curve of the effects of each compound on the Porsolt forced swim test as assessed by the rats' response (reduced floating time) during a 5-minute swimming test.

Male 2-3 month old Sprague Dawley rats were used (Harlan, Indianapolis, Ind.). Rats were housed in Lucite cages with aspen wood chip bedding, maintained on a 12:12 light:dark cycle (lights on at 5 AM), and given ad libitum access to Purina lab chow (USA) and tap water throughout the study.

The Porsolt forced swim test adapted for use in rats was performed as described by Burgdorf et al., (The long-lasting antidepressant effects of rapastinel (GLYX-13) are associated with a metaplasticity process in the medial prefrontal cortex and hippocampus. Neuroscience 308:202-211, 2015). Animals were placed in a 46 cm tall×20 cm in diameter clear glass tube filled to 30 cm with tap water (23±1° C.) for 15 min on the first day (habituation) and 5 min on the subsequent test day. Animals were tested 1 h post-dosing with the compounds (Compound A and Compound B), positive control (Compound D, 10 µg/kg), or vehicle (0.5% sodium carboxymethyl cellulose (Na-CMC) in 0.9% sterile saline). Water was changed after every other animal. Animals were videotaped, and floating time as defined as the minimal amount of effort required to keep the animals head above water was scored offline by a blinded experimenter with high inter-rater reliability (Pearson's r>0.9).

The $EC_{50}$ was defined as the dose (or log linear interpolation of dose) that exhibited a half maximal effect (average of the vehicle and maximally efficacious dose) from a log (dose) linear plot. The maximally efficacious dose was defined as the lowest dose that was statistically different from vehicle but statistically equivalent (per Fisher's PLSD) to the higher doses.

Figure 17:
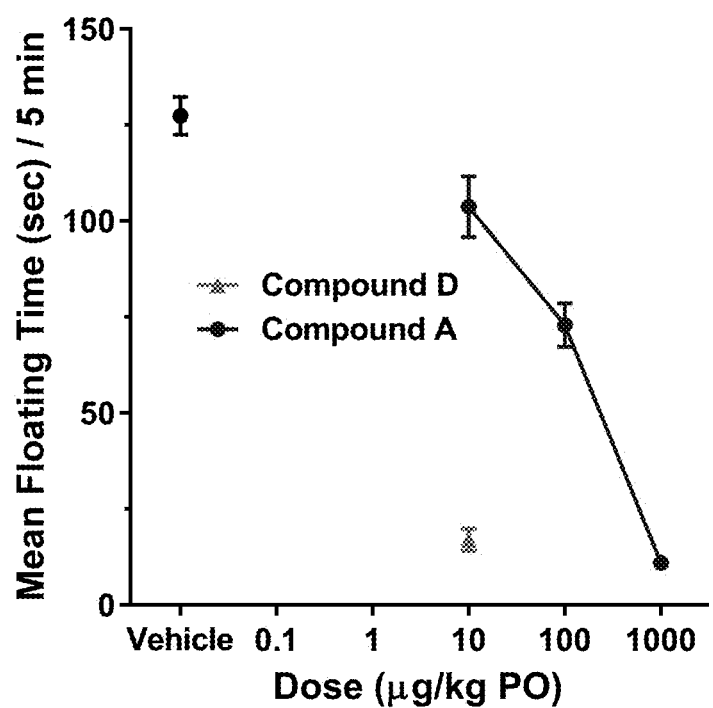
FIG. 17 depicts the results from the Porsolt forced swim test for Compound A.

The results for Compound A are shown in FIG. 17. Adult male Sprague Dawley rats were dosed with Compound A (10-1000 µg/kg PO; blue circles or data points connected via lines), positive control Compound D (10 µg/kg PO; green circle or the data point at 10 µg/kg PO), or Na-CMC in 0.9% saline (1 ml/kg PO; black circles or data point at 1 ml/kg PO) 1 h before testing. Mean±SEM floating time in the rat Porsolt test is shown. Animals received a 15 min habituation session 1 day before the 5 min test. N=6-18 per group. As shown, Compound A produces an antidepressant-like effect as measured by decreased floating time in the Porsolt test compared to vehicle group 1 h post-dosing.

Figure 18:
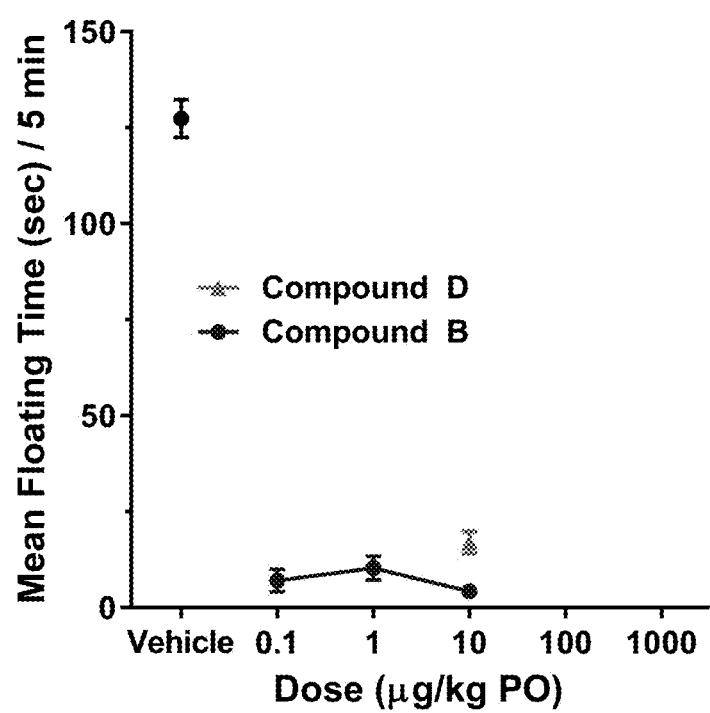
FIG. 18 depicts the results from the Porsolt forced swim test for Compound B.

The results for Compound B are shown in FIG. 18. Adult male Sprague Dawley rats were dosed with Compound B (0.1-10 µg/kg PO; blue circles or data points linked with line), positive control Compound D (10 µg/kg PO; green circle or data point at 10 µg/kg PO), or Na-CMC in 0.9% saline (1 ml/kg PO; black circles or data point at 1 ml/kg PO) 1 h before testing. Mean±SEM floating time in the rat Porsolt test is shown. Animals received a 15 min habituation session 1 day before the 5 min test. N=6-18 per group. As shown, Compound B produces an antidepressant-like effect as measured by decreased floating time in the Porsolt test compared to vehicle group 1 hour post-dosing.

Example 17

The table below shows comparative in-vivo binding data for wild-type NMDAR2 subtypes in the presence of Compound A, Compound B, tert-butyl (R)-2-((2S,3R)-1-amino-3-hydroxy-1-oxobutan-2-yl)-1-oxo-2,5-diazaspiro[3.4]octane-5-carboxylate (Compound W), tert-butyl (S)-2-((2S,3R)-1-amino-3-hydroxy-1-oxobutan-2-yl)-1-oxo-2,5-diazaspiro[3.4]octane-5-carboxylate (Compound X), (2S,3R)-3-hydroxy-2-((R)-5-isobutyryl-1-oxo-2,5-diazaspiro[3.4]octan-2-yl)butanamide (Compound Y), or (2S,3R)-3-hydroxy-2-((S)-5-isobutyryl-1-oxo-2,5-diazaspiro[3.4]octan-2-yl)butanamide (Compound Z).

| | NMDAR2A BINDING PROFILE | | | NMDAR2B BINDING PROFILE | | |
|---|---|---|---|---|---|---|
| Compound | -logEC$_{50}$ | %1 mM Glycine | Conclusion | -logEC$_{50}$ | %1 mM Glycine | Conclusion |
| Compound W | −11.35 | 18.33 | WT2A agonist | −8.976 | 53.09 | WT2B agonist |
| Compound X | −12.01 | 41.04 | WT2A agonist | −9.833 | 59.55 | WT2B agonist |
| Compound Y | −11.05 | 61.76 | WT2A agonist | −13.36 | 70.74 | WT2B agonist |

-continued

| | NMDAR2A BINDING PROFILE | | | NMDAR2B BINDING PROFILE | | |
|---|---|---|---|---|---|---|
| Compound | -logEC$_{50}$ | %1 mM Glycine | Conclusion | -logEC$_{50}$ | %1 mM Glycine | Conclusion |
| Compound Z | −10.06 | 42.5 | WT2A agonist | −13 | 70.49 | WT2B agonist |
| Compound A | −11.34 | 47.42 | WT2A agonist | −8.51 | 68.22 | WT2B agonist |
| Compound B | −9.01 | 24.48 | WT2A agonist | −13.11 | 49.02 | WT2B agonist |

| | NMDAR2C BINDING PROFILE | | | NMDAR2D BINDING PROFILE | | |
|---|---|---|---|---|---|---|
| Compound | -logEC$_{50}$ | %1 mM Glycine | Conclusion | -logEC$_{50}$ | %1 mM Glycine | Conclusion |
| Compound W | −9.839 | 67.5 | WT2C agonist | −11.15 | 66.72 | WT2D agonist |
| Compound X | −12.9 | 59.73 | WT2C agonist | −11.88 | 93.58 | WT2D agonist |
| Compound Y | −11.44 | 64.24 | WT2C agonist | −9.999 | 54.85 | WT2D agonist |
| Compound Z | −11.5 | 47.76 | WT2C agonist | −11.22 | 65.32 | WT2D agonist |
| Compound A | −8.822 | 66.21 | WT2C agonist | 0 | 0 | WT2D no activity |
| Compound B | −13.02 | 85.37 | WT2C agonist | −8.4 | 66.21 | WT2D agonist |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound having the formula:

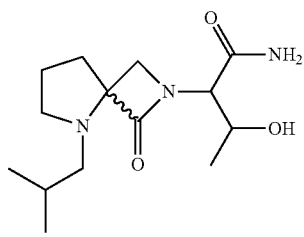 [SMILES: CC(C)CN1CCCC12CN(C(C(N)=O)C(C)O)C2=O]

or a stereoisomer, an N-oxide, and/or a pharmaceutically acceptable salt thereof.

2. The compound of claim 1 having the formula:

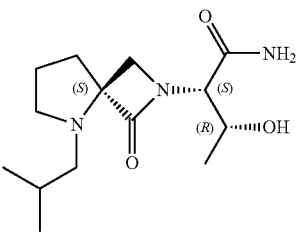

or an N-oxide and/or a pharmaceutically acceptable salt thereof.

3. The compound of claim 1 having the formula:

or an N-oxide or a pharmaceutically acceptable salt thereof.

4. A pharmaceutical composition comprising the compound of claim 1; and a pharmaceutically acceptable excipient.

5. The pharmaceutical composition of claim 4, suitable for oral administration.

6. The pharmaceutical composition of claim 4, suitable for intravenous, intranasal, subcutaneous, and/or sublingual administration.

* * * * *